United States Patent [19]
Zarling et al.

[11] Patent Number: 5,719,023
[45] Date of Patent: *Feb. 17, 1998

[54] IN SITU HYBRIDIZATION METHOD

[75] Inventors: David A. Zarling, Menlo Park; Cornelia J. Calhoun, San Francisco; Elissa P. Sena, Palo Alto, all of Calif.

[73] Assignee: Daikin Industries, Ltd., Osaka, Japan

[*] Notice: The term of this patent shall not extend beyond the expiration date of Pat. No. 5,506,098.

[21] Appl. No.: 199,326

[22] PCT Filed: Sep. 3, 1992

[86] PCT No.: PCT/JP92/01128

§ 371 Date: Jun. 3, 1994

§ 102(e) Date: Jun. 3, 1994

[87] PCT Pub. No.: WO93/05177

PCT Pub. Date: Mar. 18, 1993

Related U.S. Application Data

[63] Continuation-in-part of Ser. No. 755,291, Sep. 4, 1991, Pat. No. 5,506,098.

[51] Int. Cl.$^6$ .............................. C12Q 1/68; C12Q 1/70
[52] U.S. Cl. ........................................... 435/6; 435/5
[58] Field of Search ....................... 435/5, 6; 935/77, 935/78

[56] References Cited

U.S. PATENT DOCUMENTS

| | | | |
|---|---|---|---|
| 4,683,202 | 7/1987 | Mullis | 435/91.2 |
| 4,888,274 | 12/1989 | Radding et al. | 435/6 |

FOREIGN PATENT DOCUMENTS

| | | |
|---|---|---|
| 0 322 311 | 12/1988 | European Pat. Off. |
| WO85/05685 | 12/1985 | WIPO |
| WO87/01730 | 3/1987 | WIPO |
| WO91/17267 | 11/1991 | WIPO |

OTHER PUBLICATIONS

Di Capua, E., et al., "Characterization of Complexes between recA Protein and Duplex DNA by Electron Microscopy," *M. Mol. Biol.* 157: 87–103 (1982).

Fan, Y.-S., et al., "Mapping small DNA sequences by fluorescence *in situ* hybridization directly on banded metaphase chromosomes," *Proc. Natl. Acad. Sci. USA* 87: 6223–6227 (1990).

Honigberg, S.M., et al., "Ability of RecA protein in promote a search for rare sequences in duplex DNA," *Proc. Natl. Acad. Sci. USA* 83: 9586–9590 (1986).

Infantolino, D., et al., "HBV–DNA by *in situ* hybridization. A method to improve sensitivity on formalin–fixed, paraffin–embedded liver biopsies," *Liver* 9: 360–366 (1989).

Saiki, R.K., et al., "Enzymatic Amplification of β–Globin Genomic Sequences and Restriction Site Analysis for Diagnosis of Sickle Cell Anemia," *Science* 230: 1350–1354 (1985).

Griffith et al., "Intercalating Drugs Markedly Affect the Ability of the *E. coli* RecA Protein to Insert Small Primers Into Homologous Duplex DNA," *J. Cell Biochem.* (Suppl. 13E, 287) (1989).

Koch et al., "Oligonucleotide–priming methods for the chromosome–specific labelling of alpha satellite DNA in situ," *Chromosoma* 98:259–265 (1989).

Haase et al., "Amplification and detection of lentiviral DNA inside cells," *PNAS* 87:4981–4975 (1990).

Weier et al., "Two–color hybridization with high complexity . . . ," *Chromosoma* 100:371–376 (1991).

Van Dekken, H., et al., "Three–dimensional analysis of the organization of human chromosomes domains in human and human–hamster hybrid interphase nuclei," *Journal of Cell Science* 94:299–306 (1989).

*Primary Examiner*—Eggerton A. Campbell
*Attorney, Agent, or Firm*—Gary R. Fabian; LeeAnn Gorthey

[57] ABSTRACT

A method of identifying the presence of a known target sequence in nucleic acid contained in a fixed cellular or subcellular biological structure. By adding a stable, reporter-labeled RecA/single-stranded probe complex to the cellular or subcellular structure, the target sequence can be effectively labeled by in situ hybridization, allowing the target sequence to be visualized histologically and microscopically or detected by in situ cytometry or cell sorting flow techniques.

44 Claims, 13 Drawing Sheets

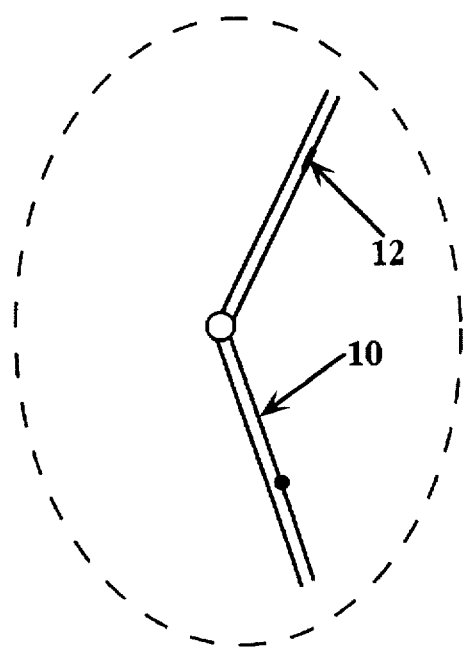
Fig. 4A
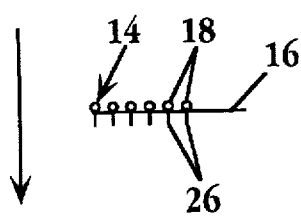
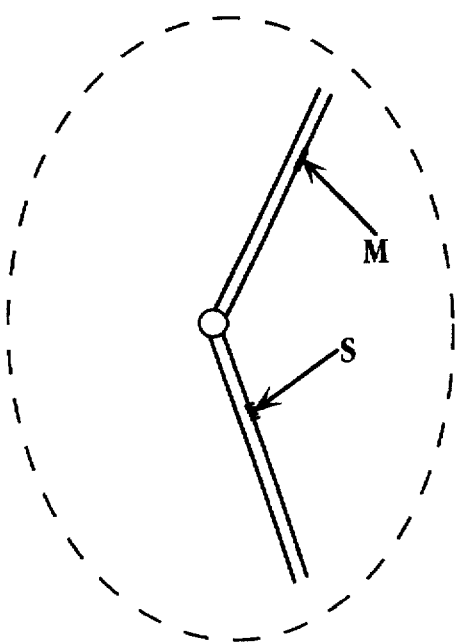
Fig. 4B
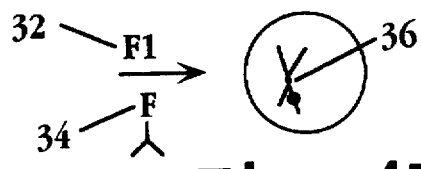
Fig. 4C
Fig. 4D

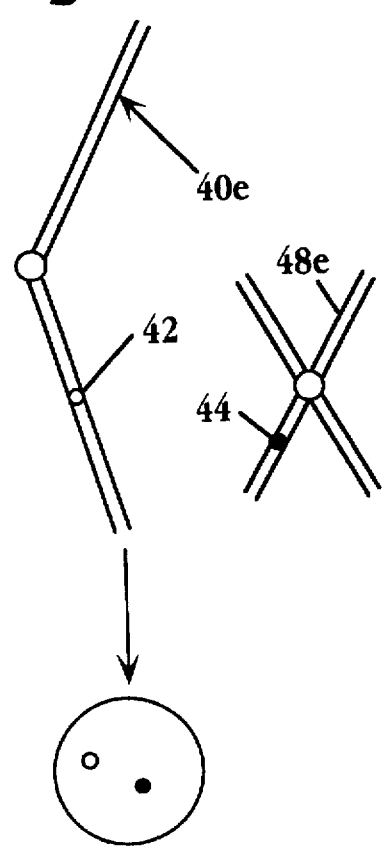
Fig. 9A
Fig. 9B
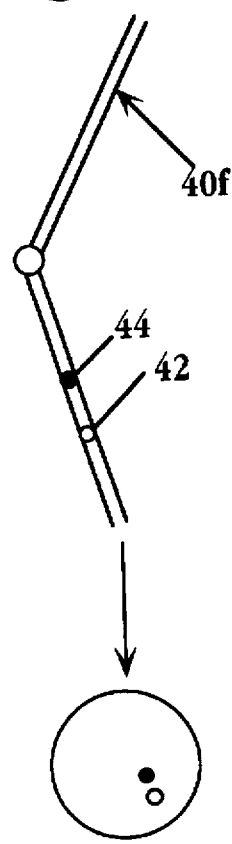
Fig. 10A
Fig. 10B
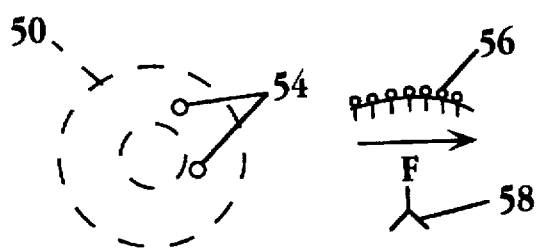
Fig. 11A
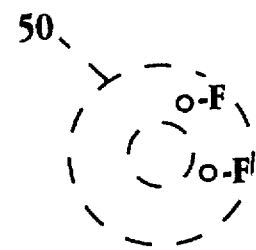
Fig. 11B
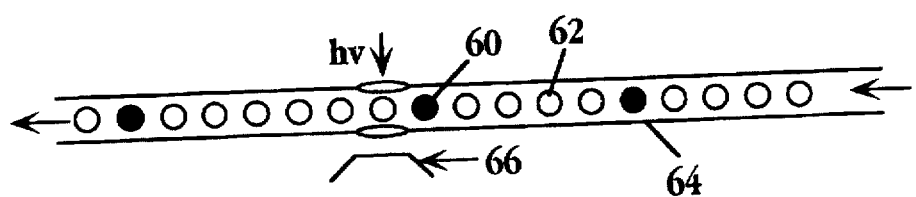
Fig. 11C

IN SITU HYBRIDIZATION METHOD

This application is the national stage of PCT/JP92/01128, filed on Sep. 2, 1992, which a continuation-in-part of co-owned, U.S. application Ser. No. 07/755,291, filed 4 Sep. 1991.

1. FIELD OF THE INVENTION

The present invention relates to a diagnostic method for performing in situ hybridization with double-stranded DNA targets.

2. REFERENCES

Alexandrov, S. P. M., et al., Chromosoma, 96:443 (1988).
Baan, R. A., et al., Prog Clin Biol Res 340A:101 (1990).
Blum, H. E., et al., Lancet, 771 (1984).
Blum, H. E., et al., Virology, 139:87 (1984).
Buchbinder, A., et al., J of Virol Methods, 21:191 (1988).
Chen, T. R., Cytogenet Cell Genet 48:19 (1988).
Cheng, S., et al., J. Biol. Chem. 263:15110 (1988).
Cherif, D., et al., Human Genetics 81:358 (1989).
Cooke, H. J., et al., Nucleic Acids Res. 6:3177 (1979).
Disteche, C. M., et al., Cytometry 11:119 (1990).
Emmerich, P., et al., Exp Cell Res 181:126 (1989).
Fujiyama, A., et al., Nucleic Acids Res. 11:4601 (1983).
Galbert, F., et al., Nature 281:646 (1979).
Griffith, et al., Biochem. 24:158 (1985).
Haase, A. T., et al., Virology, 140:201 (1985).
Haase, A. T., et al., Proc Natl Acad Sci USA, 87:4971 (1990).
Harders, J., et al., EMBO J, 8(13):3941 (1989).
Joseph, A., et al., Exp Cell Res, 183:494 (1989).
Keller, G. H., et al., Anal. Biochem, 170:441 (1988).
Kitazawa, S., et al., Histochemistry, 92:195 (1989).
Korba, B. E., et al., Virology, 165:172 (1988).
Korenberg, J. R., et al., Cell, 53:391 (1988).
Lawrence, J. B., et al., Cell, 52:51 (1988).
Lawrence, J. B., Genome Analysis, 1:1 (1990).
Lebo, R. V., et al., Science, 225:57 (1984).
Lichter, P., et al., Science, 247:64 (1990).
Lichter, P., et al., Nature, 345:93 (1990).
Lucas, J. N., et al., Int J Radiat Biol, 56(1):35 (1989).
Madiraju, M., et al., Proc. Natl. Acad. Sci. USA, 85:6592 (1988).
McCormick, M. K., et al., Proc. Natl. Acad. Sci. USA, 86:9991 (1989).
Meyne, J., et al., Genomics 4:472 (1989).
Moyzis, R. K., et al., Proc Natl Acad Sci USA, 85:6622 (1988).
Narayanswami, S., et al., Cytometry, 11:144 (1990).
Niedobitek, G., et al., Am J of Pathology, 131(1):1 (1989).
Noonan, C. A., et al., Proc Natl Acad Sci USA, 83:5698 (1986).
Ono, Y., et al., Nucleic Acids Res. 11:1747 (1983).
Pinkel, D. et al., Proc Nat Acad Sci, 83:2934 (1986).
Shen, D., et al., Cancer Research, 48:4334 (1988).
Shibata, T., et al., J. Bio. Chem., 256:7557 (1981).
Simon, D., et al., Cytogenet Cell Genet, 39:116 (1985).
Trask, B., et al., Hum Genet 78:251 (1988).
Unger, E. R., et al., Am J of Surg Pathology, 10(1):1 (1986).
Urdea, M. S., et al., Nucl Acid Res, 16:4937 (1988).
van Dekken, H., et al., Acta histo, 37:91 (1989).
van Dekken, H., et al., Cytometry, 11:153 (1990).
van Dekken, H., et al., Cytometry, 11:579 (1990).
Weier, H., et al., BioTechniques 10(4):498 (1991).
Zischler, H., et al., Hum Genet, 82:227 (1989).

3. BACKGROUND OF THE INVENTION

In situ hybridization employs direct hybridization of a DNA probe with DNA or RNA in biological structures, typically permeabilized cells, subcellular fractions, or fixed chromosome preparations. Because the method can yield morphological information about the localization of specific-sequence target nucleic acid(s) in fixed biological structures, it is applicable to many areas of biomedical research, such as developmental biology, cell biology, genetics and particularly gene mapping, pathology and gene diagnostics.

In most applications, in situ hybridization is directed toward a target sequence in a double-stranded duplex nucleic acid, typically a DNA duplex associated with a pathogen or with a selected sequence in viral or cell chromosomal DNA. In this method, as it has been practiced heretofore, a single-stranded labeled probe is added to the permeabilized structure, which has been heated to a temperature sufficient to denature the target duplex nucleic acid, and the probe and denatured nucleic acid are allowed to react under suitable hybridization, or reannealing conditions. After removal of unbound (non-hybridized) probe, the structure is processed for examination for the presence of reporter label, allowing the site(s) of probe binding to target duplex nucleic acid to be localized in the biological structure, i.e., in the context of cell or subcellular morphology.

The method has been widely applied to chromosomal DNA, for mapping the location of specific gene sequences, and distances between known gene sequences (Lichter, Meyne, Shen), for studying chromosomal distribution of satellite or repeated DNA (Weier, Narayanswami, Meyne, Moyzis, Joseph, Alexandrov), for examining nuclear organization (Lawrence, Disteche, Trask), for analyzing chromosomal aberrations (Lucas), for localizing DNA damage in single cells or tissue (Baan) and for determining chromosome content by flow cytometric analysis (Trask). Several studies have reported on the localization of viral sequences integrated into host-cell chromosomes (e.g., Harders, Lawrence, Lichter, Korba, Simon). The method has also been used to study the position of chromosomes, by three-dimensional reconstruction of sectioned nuclei (van Dekken), and by double in situ hybridization with mercurated and biotinylated probes, using digital image analysis to study interphase chromosome topography (Emmerich).

Another general application of the in situ hybridization method is for detecting the presence of virus in host cells, as a diagnostic tool (Unger, Haase, Noonan, Niedobitek, Blum). In certain cases where the number of virus particles in the infected cell is very low, it may be necessary to first amplify viral sequences by in situ adopted polymerase chain reaction (PCR) methods (Haase, 1990, Buchbinder).

The in situ hybridization method described above has a number of limitations. The most serious limitation is the requirement for denaturing the duplex target DNA, to form the necessary single-stranded form of the target. Denaturation typically is performed by heating the sample or treating with chemicals and heat. The heat treatment can produce spurious and unwanted changes in the nucleic acid being examined, related to structural changes and nucleic acid reassociation with repeated sequences within the DNA. The repeated DNA sequences can randomly reassociate with one another. The step also adds to the time and effort required in the method.

Secondly, where the target sequence of interest is present in very low copy number, the method is limited, by renaturation kinetics, to long renaturation times. Even then, the method may be incapable of producing probe/target renaturation events at low target concentration. This limitation may be partly overcome, as indicated above, by first amplifying the target duplex in situ by modified PCR methods. However, the PCR approach involves additional steps, and may be unsuitable for many in situ studies, such as those involving localization of genomic chromosomal DNA sequences.

4. SUMMARY OF THE INVENTION

It is therefore a general object of the present invention to provide an in situ hybridization method, for use in detecting and/or localizing target nucleic acid, typically duplex DNA, in a fixed biological structure, which (a) does not require heat denaturation of the target duplex, and (b) is not limited in target duplex copy number by renaturation kinetics.

The present invention includes a method of identifying the presence of a known target sequence in a double-stranded nucleic acid contained in a cellular or subcellular biological structure, in a specific morphological relationship with the structure. The method includes adding to the structure, a probe complex composed of RecA protein stably bound to a single-stranded, reporter-labeled nucleic acid probe which is complementary to one of the strands of the duplex target sequence, under conditions in which the complex can contact the duplex nucleic acid. The complex is allowed to bind to the target sequence under non-denaturing conditions. After removing unbound complex, the structure is examined for the presence of the reporter-labeled probe bound to the nucleic acid.

The complex is preferably stabilized by preparation in the presence of ATPγS. The probe may be labeled with a detectable reporter, such as a radiolabel, enzyme or fluorescence tag, or with a ligand, such as biotin or digoxigenin, which can be subsequently reacted with a reporter molecule specific for the ligand, and carrying a detectable reporter. The complex may also be stabilized using other cofactors including, but not limited to, ATPγS, GTPγS, ATP, dATP and a combination of ATPγS and ADP.

In one general application, the method is used for detection and localization of genomic sequence(s) in fixed chromosome DNA structure(s) in metaphase spreads. In one embodiment, the microscopic ultrastructure of the chromosomes is determined, for example, by fluorescence microscopy, using fluorescence banding patterns. The location of the bound complex in relation to the known ultrastructure is then determined independently, for example, by a fluorescence-labeled probe complex whose fluorescence excitation wavelength is different from that of the chromosome banding fluorescence. Alternatively, fixed cells or cellular structures are probed in suspension followed by flow cytometric or microscopic analysis.

In another general application, the method can be used for detecting the presence of virus or integrated virus-specific genomic sequences in a host cell. The binding of a fluorescence-labeled probe to the virus sequence may be determined by fluorescent microscopy or fluorescence activated cell sorting (FACS) or a light or fluorescent or laser scanning microscope. Where an enzyme label is used a light microscope can be used to visualize colored (e.g., black) peroxidase or alkaline phosphatase product produced by the reporter enzyme.

Another embodiment of the present invention includes a method of identifying the presence of a known viral nucleic acid target sequence contained in a fixed cellular or subcellular biological structure. Such known viral nucleic acid targets include known DNA viruses (such as hepatitis B virus) or RNA viruses that can have a detectable duplex virus) nucleic acid phase in their life cycle. In this method, the fixed structures or substructures can be incubated in 10 mM Tris-acetate buffer, pH7.5, at 55°–60° C. before the addition of the RecA probe complex in order to increase reaction efficiency; this step does not denature the cellular DNAs.

The present invention also includes a method of detecting a single copy nucleic acid sequence, typically a duplex DNA sequence, contained in a cellular or subcellular biological structure. In this method the cellular or subcellular biological structure(s) are fixed. A probe complex (composed of RecA protein stably bound to a single-stranded, reporter-labeled probe which is complementary the single-copy nucleic acid target sequence) is added to the cellular structure or substructure under conditions in which the complex can contact the nucleic acid target sequence. The complex is then allowed to bind to the target sequence under non-denaturing conditions. Unbound complex is then removed from the structure and the structure is examined for the presence of the reporter-labeled probe bound to the nucleic acid.

In this method of single-copy nucleic acid detection, the cellular structures or substructures can be fixed and analyzed in solution or on slides. The fixing can also include incubatation of the fixed structures or substructures in 10 mM Tris-acetate buffer, pH7.5, at 55°–60° C. In the method of the present invention, the complex can be bound to the target sequence under non-denaturing conditions in reactions carried out for less than 2 hours.

The method of the present invention can also include the addition of accessory proteins, such as single-strand binding protein (SSB), topoisomerase I or topoisomerase II.

The present invention also includes kits containing components useful to carrying out the methods described above. One example for a kit for in situ detection of a known viral nucleic acid in a sample may include (i) a probe derived from the viral DNA sequences, (ii) RecA protein effective for coating the probe, and (iii) means of detecting the binding of the probe to the known viral DNA in a sample. Such kits may also include RecA-protein coated DNA.

These and other objects and features of the invention will become more fully apparent when the following detailed description of the invention is read in conjunction with the accompanying drawings.

BRIEF DESCRIPTION OF THE FIGURES

FIGS. 4A–4D illustrate steps for gene localization on a chromosome, employing the method of the invention;

FIGS. 5–10 show various types of chromosomal aberrations (upper frames A), and the corresponding fluorescence pattern which would be seen with such aberrations (lower frames B); and FIGS. 11A–11C illustrate the steps in detecting virus infection of cells, by fluorescence activated cell sorting, in accordance with the invention.

6. DETAILED DESCRIPTION OF THE INVENTION

I. In situ Hybridization Method

Figure 1A:
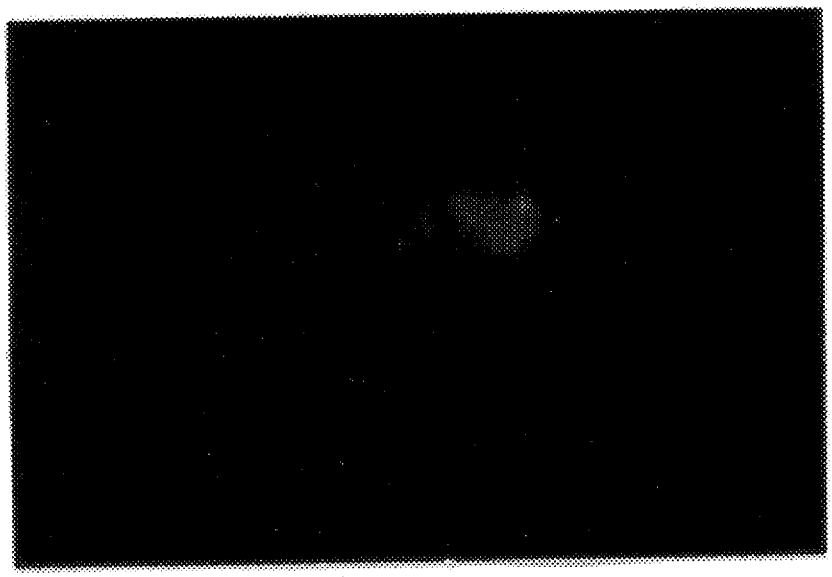
FIGS. 1A and 1B are fluorescence photomicrographs of chromosome X alpha satellite DNA probe used for detection of decondensed or partially decondensed alpha satellite chromosomal centromeric DNA target sequences in native, nondenatured (1A) and heat-denatured (1B) methanol-acetic acid fixed interphase HEp-2 cell nuclei.

This section describes the basic methodology of in situ hybridization, in accordance with the invention, as applied to various biological structures containing a duplex DNA target with a repeated or unique specific basepair sequence.

A. Preparation of Biological Structures for DNA Detection

The method of the invention is designed for detecting, by complementary-basepair hybridization, a selected target sequence in a biological structure contain a duplex nucleic acid, usually a DNA/DNA duplex nucleic acid. The biological structure is any morphologically distinct structure, such as a cell, sperm, parasite, subcellular fraction or chromosomal preparation containing the target nucleic acid.

The target duplex in the structure is typically chromosomal DNA, or nucleic acid duplex material associated with a viral, parasitic or bacterial pathogen, such as virus particles composed of viral duplex genome encapsulated or released from being encapsulated in viral coat proteins. Methods of preparing fixed biological structures, such as cells, nuclei, and chromosomal preparations generally follow those used in conventional in situ hybridization by DNA duplex denaturation and reannealing.

Briefly, the cellular compartment and DNA structure may be further fixed or permeabilized by treatment with an organic solvent and acid or cross-linking agent to fix the structural components in their natural morphological relationship. Common fixatives include acetic acid, salts, methanol, formalin, paraformaldehyde, and glutaraldehyde. After fixation, tissue sample may be prepared for slide presentation by embedding in wax or by freezing, followed by sectioning into thin slices.

More generally, the biological material is treated with one or more of a number of agents capable of deproteinizing and/or delipidizing the structures. Such methods can involve the use of proteases, lipases, acid, organic solvents including alcohols, detergents or heat denaturation or combinations of these treatments. A common treatment involves one or more washes with methanol:acetic acid.

Other pretreatments may be useful in reducing background, such as use of inhibitors of non-specific binding of nucleic acids. For example, prehybridization with non-specific carrier DNA (e.g. salmon sperm) or RNA (e.g. tRNA), may act to reduce non-specific probe binding to the fixed DNA-target structure.

Cellular structures of interest may be individual cells, obtained for example from cell culture, cells present in a tissue section or body fluid. Typically, cellular structures from a tissue are sectioned cryogenically, then treated on a slide, as above, to permeabilize the section, such as by treatment with methanol:acetic acid. Cellular structures may be studied to determine intracellular localization of genomic target sequence(s), or for detecting the presence and/or localization of an infective organism, such as virus, bacteria, or parasite in the cells.

Subcellular structures, such as nuclei and mitochondria, can be prepared by conventional fractionation methods, such as isopycnic centrifugation, to obtain subcellular material in enriched or substantially purified form. Thereafter, the enriched structure preparation may be permeabilized and deproteinized, as above, probed either in solution or affixed to a slide, as by drying.

Alternatively, the cells may be pretreated with 75 mM KCl, followed by treatment with methanol:acetic acid, to remove cytoplasm. This fraction, after purification may be further treated for probe hybridization. This method is illustrated in Examples 3–4 and 12–14 for the preparation of HEp-2 cell nuclei for in situ hybridization.

Briefly in these examples, HEp-2 cells were pelleted by low-speed centrifugation and the pellet was resuspended in 75 mM KCl for between 5 and 15 min for a desired amount of nuclear swelling to occur, followed by addition of ice cold methanol:acetic acid and centrifugation. After general further addition of ice cold methanol:acetic acid and gentle agitation of the cells after each addition followed by centrifugation, cytoplasm was degraded from the nuclei. The resulting isolated nuclei preparation was resuspended in methanol:acetic acid, placed in 10 μl aliquots on microscope slides, dried, and the slides stored at −20° C. for later use. Alternatively, cells can be harvested using standard conditions, washed in 1× phosphate buffered saline (PBS) and fixed in 100% methanol or 70% ethanol then stored at −20° C.: these cells can be used in solution hybridization detection reactions.

Another structure of general interest is a fixed chromosome preparation, typically derived from cells in metaphase (Pinkel, Cherif). The preparation may contain the entire set of genomic chromosomes from the cell, such as the preparation in FIGS. 1A and 1B, or individual, isolated chromosomes, such as can be obtained by published methods (Lebo, McCormick) or chromosome fragments. The chromosomes are generally treated with methanol:acetic acid, placed on a slide, then affixed to the slide with drying.

A variety of other subcellular structures, such as mitochondria, or pathogenic structures including parasites isolated from cell or blood samples, such as virion particles, may also be prepared according to standard methods, and fixed and permeabilized for in situ hybridization as above.

B. Target-Specific DNA Probe

The probe used in the method is a single-stranded nucleic acid, usually a DNA strand probe, or derived by denaturation of a duplex probe, which is complementary to one (or both) strand(s) of the target duplex nucleic acid. The probe sequence preferably contains at least 90–95% sequence homology with the target sequence, to insure sequence-specific hybridization of probe and target. The single-stranded probe is typically about 100–600 bases long, although a shorter or longer polynucleotide probe may also be employed.

The probe may be constructed or obtained by one of a number of standard methods. Many probes, such as various satellite DNA sequences are commercially available in single-stranded or double-stranded form. Other probes can be obtained either directly from viruses, plasmids and cosmids or other vectors carrying specific sequences, or, if desired, by restriction digest of the source of the probe DNA, such as a vector, followed by electrophoretic isolation of specific restriction digestion fragments. Probes obtained in this manner are typically in double-stranded form, but may, if required, be subcloned in single-stranded vectors, such as an M13 phage vector.

Alternatively, the probe may be prepared in single-stranded form by oligonucleotide synthesis methods, which may require, for larger probes, forming subfragments of the probe, then piecing the subfragments together.

The probe is labeled with a reporter or ligand or moiety which allows detection of the targeted sequence in situ. For autoradiographic detection, the reporter is a radiolabel, such as $^{32}$P-labeled probe formed, for example by nick translation or polymerase chain reaction in the presence of labeled nucleotides.

For fluorescence detection, the probe may be labeled with one of a selection of fluorescence groups, such as FITC, BODIPY, Texas Red, or Cascade Blue which is excitable in a specific wavelength, such as 490, 540, and 361 nm. The groups are derivatized to 3' or 5' probe ends or by incorporation or reaction at internal positions, according to standard methods (Urdea, Keller, Zischler).

Alternatively, the probes may be labeled with a ligand-type reporter: such as biotin (Weier), digoxigenin (Zischler), or bromodeoxyuridine (BrdUrd) or other modified bases including fluorescein-11-dUTP (Boehringer-Mannheim) (Kitazawa). The probe reporter groups are detected, in situ, by reaction of the hybridized probe with a secondary reporter molecule which (a) binds specifically and with high affinity to the probe ligands, and (b) contains a detectable reporter. The binding moiety of the secondary molecule may be avidin or streptavidin, for binding to biotinylated nucleotides, anti-digoxigenin antibody, for binding to digoxigenin-labeled nucleotides, and anti-BrdUrd antibody for binding to BrdUrd-labeled probe.

The detectable reporter in the secondary molecule is typically a fluorescence label, but may also be a radiolabel, for autoradiographic detection, an antibody, an enzyme, for colorimeteric or chemiluminescence detection in the presence of a suitable substrate, or colloidal gold (Narayanswami) for use in electron microscopic visualization.

C. RecA and mutant RecA803 protein purification

RecA and RecA803 proteins, for use in forming the RecA/probe complex used in the invention, are preferably isolated from overproducing strains, such as E. coli strains JC12772 and JC15369 (obtained from A. J. Clark and M. Madiraju). These strains contain the RecA coding sequences on a "runaway" replicating plasmid vector present at high copy numbers per cell. The RecA803 protein is a high-activity mutant of wildtype RecA (Madiraju).

The RecA proteins can be purchased from Pharmacia or purified using fast protein liquid chromatography (FPLC) on a hydroxylapatite column followed by an anion (Mono®Q) exchange column. The isolation procedure combines and modifies published procedures (Shibata et al., Griffith). Details are provided in Example 1.

The standard assays for monitoring the protein purification include assay of 30,000-dalton RecA protein by SDS-polyacrylamide gel electrophoresis (PAGE) (Pharmacia Phastgel system), enzyme assay of ssDNA-dependent ATPase activity using [γ-$^{32}$P] ATP and cellulose thin-layer chromatography developed in a solvent of 0.5M LiCl and 0.25M formic acid, assay of DNase, assay of D-loop activity with 500-mer oligonucleotide probe.

Analysis of total protein from JC12772 and JC15369 cell extracts by SDS-PAGE (denaturing conditions) shows that the 30,000-dalton RecA protein is the major protein produced in these strains.

The SDS-PAGE profiles of the final Mono-Q-purified RecA and RecA803 proteins showed a single 30,000-dalton band, free of other cellular polypeptides as detected by silver staining.

D. Preparation of RecA DNA Probe Complexes

The duplex nucleic acid in the biological structure of interest is reacted with a probe complex composed of RecA protein stably bound to the single-stranded probe. The complex is preferably prepared in a stabilized form in the presence of ATPγS.

RecA protein coating of probes is normally carried out as detailed in Example 2. Briefly, the probe, whether double-stranded or single-stranded, is denatured by heating at 95°–100° C. for five minutes, then placed in an ice bath for 20 seconds to one minute followed by centrifugation at 0° C. for approximately 20 sec, before use. Denatured probes can placed in a freezer at –20° C.; preferably, however, they are immediately added to standard RecA coating reaction buffer containing ATPγS, at room temperature, and to this is added the RecA protein.

ReCA coating of probe is initiated by incubating probe-RecA mixtures at 37° C. for 10–15 min. RecA protein concentration tested during reaction with probe varies depending upon probe size and the amount of added probe, and preferably ranges between about 2 to 25 μM. When single-stranded probes are RecA coated independently of their homologous probe strands, the mM and μM concentrations of ATPγS and RecA, respectively, can be reduced to one-half those used with double-stranded probes (i.e. ReCA and ATPγS concentration ratios are usually kept constant at a specific concentration of individual probe strand, depending on whether a single- or double-stranded probe is used).

E. Probe Hybridization to Permeabilized Biological Structures

According to an important feature of the invention, sequence-specific binding of the RecA/probe complex to the target duplex contained in a biological structure is achieved by adding the probe complex to the structure, under non-denaturing conditions, i.e., below the denaturation temperature of the duplex DNA, and allowing the complex to contact the target duplex, typically for 1–4 hours at 37° C., until homologous binding of the probe complex to the target ONA sequence has occurred.

After probe binding to the target DNA sequence, the target structure is washed to remove unbound probe complex. In the usual case, where the probe reporter is a ligand, such as biotin, the washed structure is contacted with a detectable reporter molecule, such as fluorescence-labeled avidin (FITC-avidin), to bind a detectable reporter to the target-bound probe. The sample material is then further washed to remove unbound reporter molecule. A variety of wash procedures are suitable. The structure is visualized or otherwise viewed or detected by microscopy, fluorescence activated cell sorting, autoradiography, or the like, as for example described below.

The hybridization condition described in Example 3, for use in fluorescence-reporter detection of a biotinylated probe, are exemplary. Briefly, between 10–20 µl probe complex is applied to a fixed preparation on a glass slide. Glass coverslips are placed over the hybridization areas and sealed, and the reactions are incubated in a moist container in a 37° C. 7% $CO_2$ incubator for between 1–4 hours. Following incubation, the coverslip rubber cement seal is removed and the slides, with coverslips are washed several times to loosen and remove coverslips and remove unbound probe complex.

The slides are placed in preblock solution, followed by (a) immersion in or application of FITC (fluorescein isothiocyanate)-avidin, in preblock solution in the dark, then in several washes to remove unbound FITC-avidin. An antifade agent, with or without counterstain such as propidium iodide, may be used to reduce photobleaching.

If necessary the probe signal may be amplified by reacting the material on the slide with biotinylated anti-avidin antibody, followed by several wash steps and addition of FITC-avidin, to enhance the amount of fluorescent signal bound to the target duplex.

The target structure is then examined for the presence of the reporter-labeled probe bound to the target nucleic acid, e.g., by fluorescence microscopy or laser scanning microscope.

FIG. 1A shows FITC signal from in situ hybridization of a chromosome X alpha satellite DNA probe to prepared, isolated HEp-2 cell interphase nuclei fixed on glass slides, in accordance with the present invention and without amplification, following the protocol detailed in Example 3. Chromosome X is estimated to contain about 5,000 copies/cell of the alpha satellite sequences (ONCOR literature). The biotinylated probe was reacted and post-labeled with FITC-avidin, as described above.

Figure 1B:

For comparative purposes, denatured biotinylated chromosome X alpha satellite probe from the same stock used in the FIG. 1A method was combined with formamide and dextran sulfate under traditional protocols and was hybridized to HEp-2 cell nuclei using prior art thermal denaturation (and renaturation) steps, with the results shown in FIG. 1B. The procedure required several more hours for total preparation and hybridization time than the FIG. 1A method, involved signal amplification, and generally gave a lower level of fluorescent signal through the nuclei.

A second method, reported in Example 4, shows that the method gives high-probe target specificity in a low copy number target sequence, without probe signal amplification. In this method, a chromosome-7 alpha satellite DNA/RecA complex is hybridized with HEp-2 interphase nuclei, as above. Chromosome 7 contains about 10 copies of the alpha satellite sequence probe used (ONCOR®probe D7Z2).

Figure 2A:
FIGS. 2A and 2B are fluorescence photomicrographs of alpha satellite DNA probe to chromosome 7 used for detection of decondensed chromosomal centromeric DNA target sequences in native, nondenatured (2A) and heat-denatured (2B) fixed nuclei in interphase HEp-2 cells.

FIG. 2A shows the target signal pattern after probe binding and FITC labeling, in accordance with the invention. As seen, the probe is localized in two distinct spots, presumably corresponding to the two chromosome 7's containing the alpha satellite sequence.

Figure 2B:
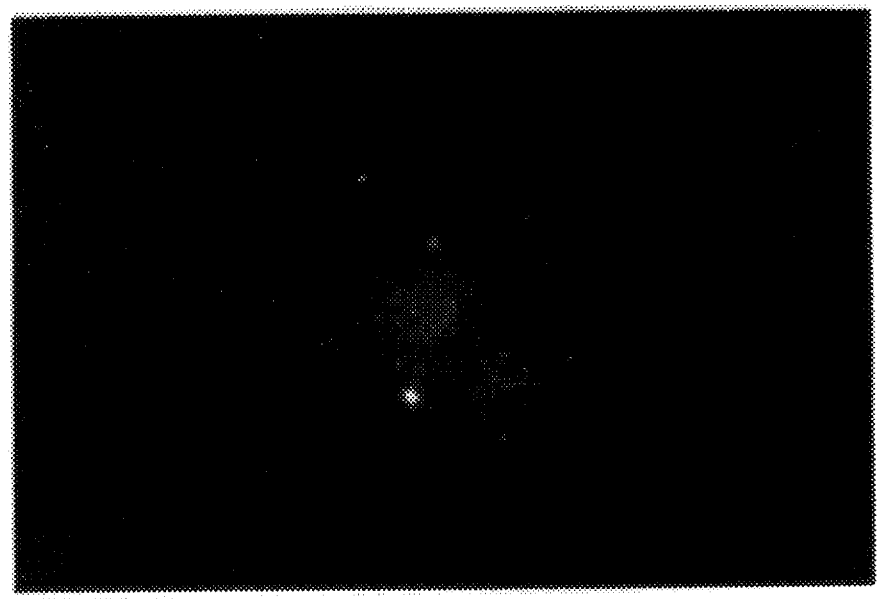

FIG. 2B shows the in situ hybridization probe bound target pattern achieved with the same probe, after amplification following prior art methods described above. Probe localization appears to be less specific than in the method of the invention. Further, total preparation and probe hybridization times were many hours longer.

Figure 3A:
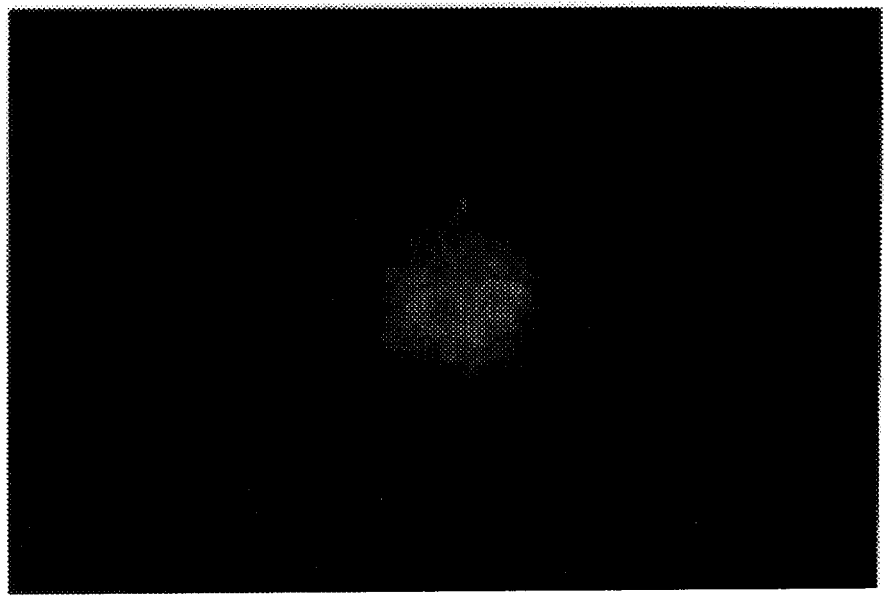
FIGS. 3A and 3B are photomicrographs taken under fluorescence microscopy (3A) and phase microscopy (3B), at the same focus, showing the distribution of chromosome X alpha satellite DNA in a dividing fixed HEp-2 cell nucleus.
Figure 3B:
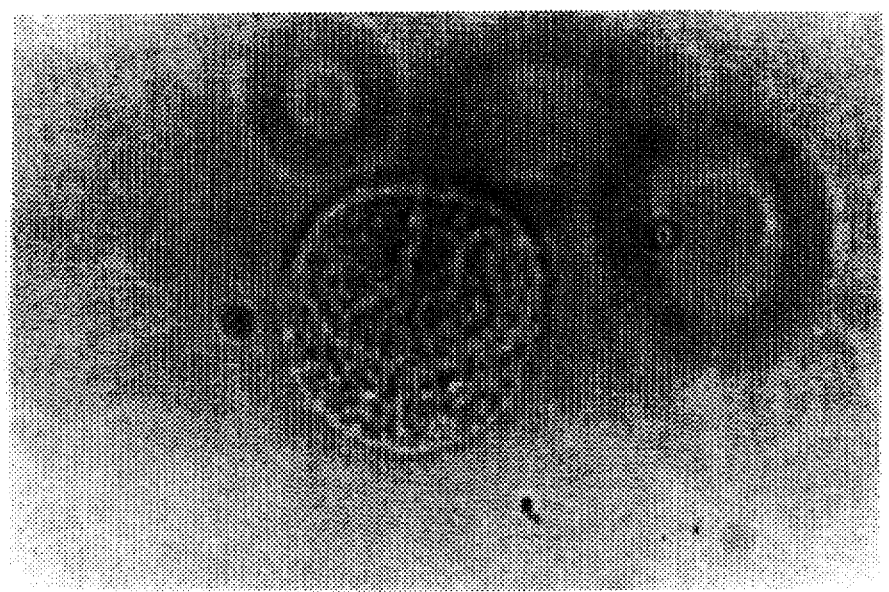

A third method, reported in Example 5, demonstrates the ability to localize a target sequence within a nuclear volume relative to other targeted DNA sequences and/or the nuclear membrane, using a confocal laser scanning microscope (Zeiss LSM-10). In this method, 100% methanol fixed HEp-2 cells were probed in suspension with the RecA/chromosome-X alpha satellite DNA probe complex, and labeled with FITC-avidin, as in FIG. 1A above. FIG. 3A shows the pattern of probe binding in a dividing nucleus. To localize the bound probe, the same field was viewed by phase contrast microscopy, without changing the focus of the lens (FIG. 3B). By examining the two photomicrographs, the relative position of the nuclear membrane and nuclear division plane can be seen with respect to the probe-labeled chromosomes.

Figure 12:
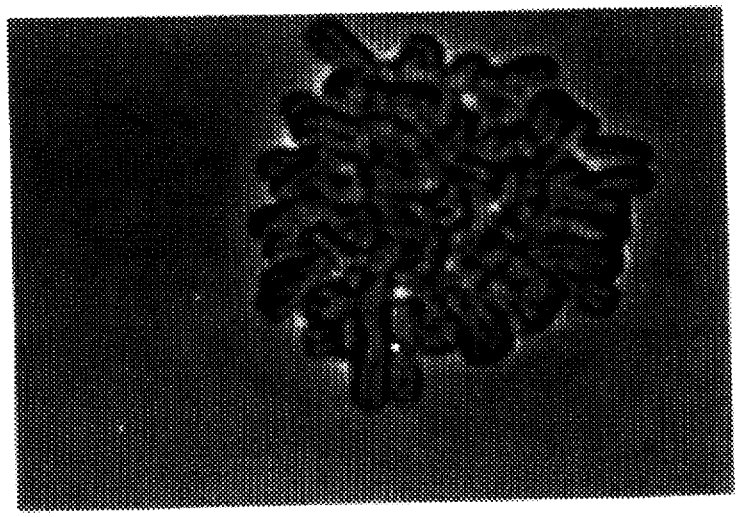
FIG. 12 presents a photograph of a cell preparation showing hybridization signal from fixed HEp-2 metaphase chromosomes hybridized with RecA-coated, biotinylated, nick-translated probe to human chromosome 1 alpha-satellite centromeric sequences.

The method of the present invention also facilitates the detection of specific DNA sequences in metaphase chromosomes using native RecA-mediated fluorescence in situ hybridization. RecA coated biotinylated probe specific for human chromosome 1 alpha-satellite centromeric sequences was reacted with fixed HEp-2 cells on slides using the native RecA-mediated fluorescence in situ hybridization (Example 6). Before RecA-coated probe mix addition, cells were incubated at 60° C. with 10 mM Tris-acetate (pH 7.5). This incubation step, below the denaturation temperature of cellular nucleic acid targets, improves the efficiency of the fluorescence in situ hybridization reaction. In Example 6, using this incubation step 73% of all cell nuclei showed fluorescence hybridization signals. FITC hybridization signals were visualized using a Zeiss LSM in 488 nm argon-ion laser-scanning mode. The FITC hybridization signal is superimposed on the phase image of the chromosomes to identify its position (FIG. 12). Note that the FITC probe signal is, as expected, located at the centromere.

Figure 13A:
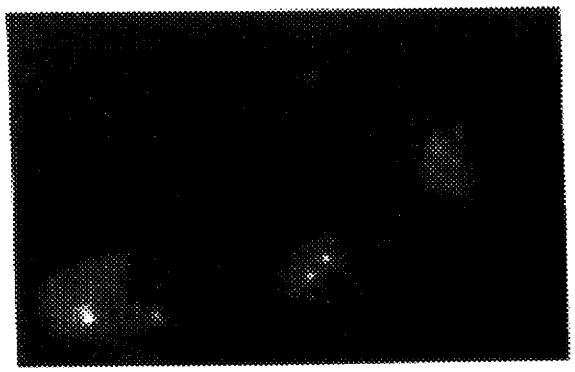
FIGS. 13A to 13F show RecA-mediated native fluorescence in situ hybridization detection of unique p53 chromosome 17 tumor suppressor gene sequences in ATCC HEp-2 and HCC "Alexander" cells in suspension.
Figure 13B:
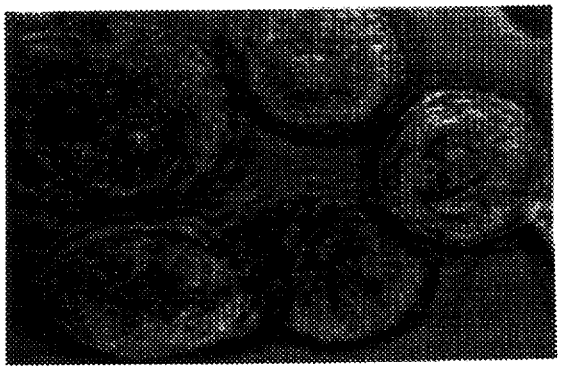
Figure 13C:
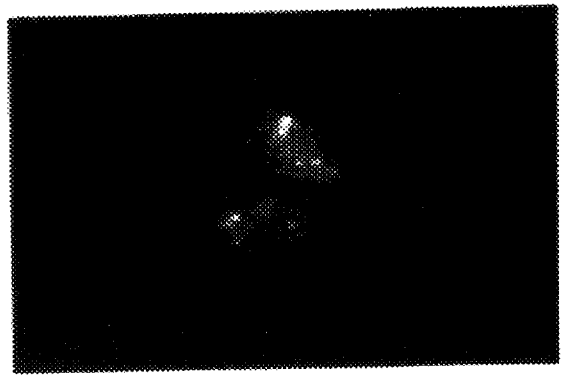
Figure 13D:
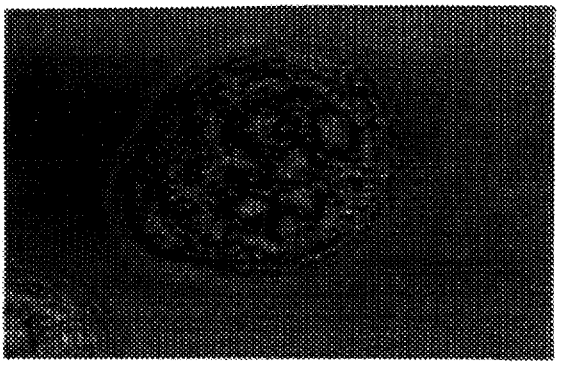
Figure 13E:
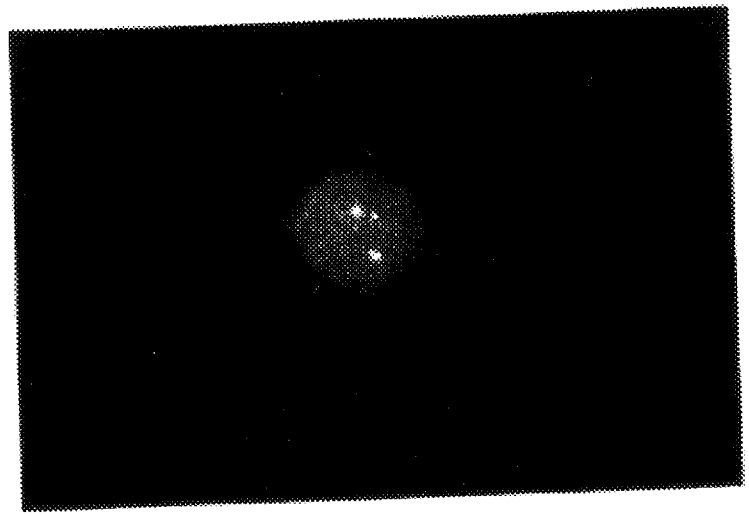
Figure 13F:
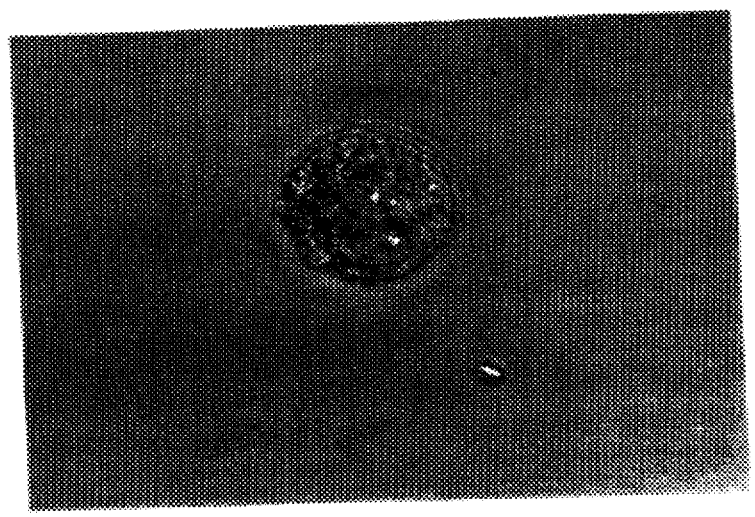
Figure 14A:
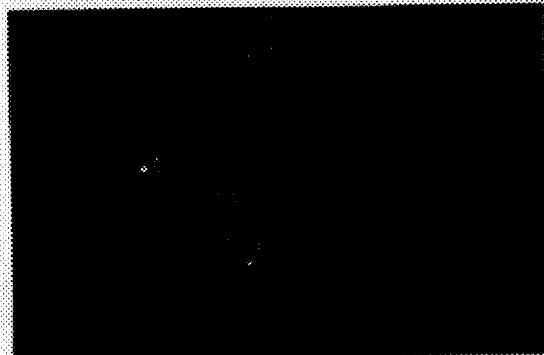
FIGS. 14A to 14D show RecA-mediated native fluorescence in situ hybridization detection of unique p53 gene sequences in ATCC HEp-2 cell nuclei on slides.
Figure 14B:
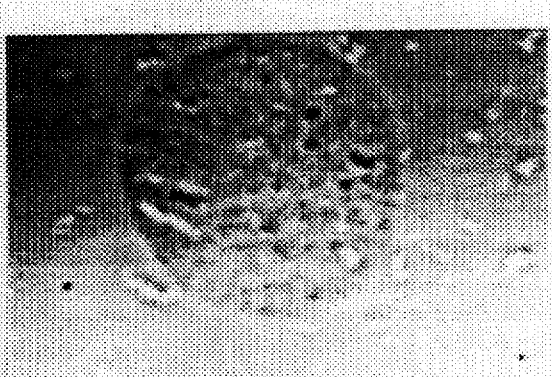
Figure 14C:
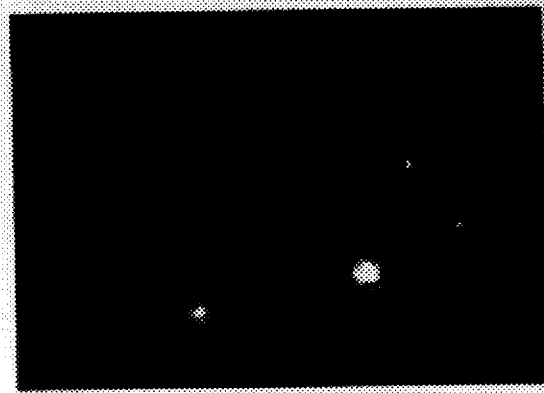
Figure 14D:
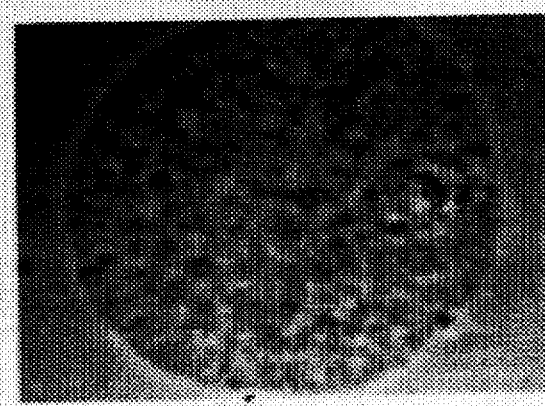

RecA-mediated fluorescence in situ hybridization also facilitates the detection of unique gone sequences. RecA-coated biotinylated probes specific for the p53 gene (Oncor) were reacted with fixed cells in suspension using native fluorescence in situ hybridization reactions (Example 7). FITC probe signals were observed with a Zeiss LSM in 488 nm argon-ion laser-scanning mode. Signals were apparent without any amplification of signal (i.e., extra signal amplification steps). The results of this analysis are presented in FIG. 13: FIG. 13A, 13C and 13E, FITC hybridization signals; FIG. 13B, 13D, and 13F, phase images of cells in 13A, 13C and 13E, respectively; FIG. 13A to 13D, HEp-2 cells; and FIG. 13E and 13F, HCC "Alexander" cells. The FITC hybridization signals in FIG. 13E are superimposed on the phase image of the cell in FIG. 13F. Note that all hybridization signals are within cell nuclei and that FITC signals are often seen as pairs indicative of newly replicated DNA. The cell nucleus in FIG. 13D appears to be in the process of dividing. The results demonstrate the sensitivity of the method of the present invention for detecting unique sequences in solution hybridization reactions.

In addition to detection of unique sequences in solution hybridization reactions, the method of the present invention is also effective for the detection of unique gene sequences using fixed cells on slides. RecA-coated biotinylated p53 probe (Oncor) was reacted with fixed HCC cells on slides using a native fluorescence in situ hybridization reaction (Example 8). This reaction contained topoisomerase II and was not incubated in buffer before probe addition (Example 8). FITC probe signals were observed with a Zeiss LSM in 488-nm laser-scanning mode. Hybridization signals were apparent without any amplification of signal (i.e., extra signal amplification steps). Sample results are presented in FIG. 14. In FIG. 14: 14A and 14C, FITC signals; 14B and 14D, phase images of cells seen in 14A and 14C, respectively. Note that all hybridization signals are within the nucleus and signals often appear as pairs. The position of the signal pairs in the nucleus shown, for example, in 14A and 14B suggests in this nucleus the signal may represent a stage after DNA replication. These results demonstrate the sensitivity of the method of the present invention for detecting unique sequences using fixed cells in hybridization reactions.

In addition to the ability of the method of the present invention to be used for the detection of unique cellular gene sequences, the method can also be used for the detection of unique viral nucleic acid sequences. RecA-coated HBV DNA probes paM6 and "BIOPROBE" were reacted with 100% methanol fixed cells in suspension using a native fluorescence in situ hybridization reaction (Example 9). Both probes used in these experiments detected HBV sequences in the human HCC cells with high efficiency ("BIOPROBE®", 81%; pAM6, 95%). FITC hybridization signals were observed with a Zeiss LSM in laser scanning mode. In FIG. 15, the observed FITC signals from the HBV probes are shown superimposed on the phase images of the cells: 15A and 15B, "BIOPROBE®", 15C–15E, pAM6 probe. Note that all signals appear to lie within the nuclear region. Both DNA probes generated multiple FITC hybridization signals in each HCC cell nucleus. The "BIO-PROBE®" signals appear less intense than the pAM6 probe signals. This is likely due to size of the probes used. A RecA-facilitated pairing reaction between single-stranded probe(s) and linear duplex target DNAs in solution increases in efficiency with increasing probe strand size: single-stranded "BIOPROBE®" strands average <250 bs and pAM6 single-strands average 300–500 bases in size. This difference might also be due to the fact that the probes contain HBV gnenomes of different serotypes ("BIOPROBE®", adr-4; pAM6, adw). These results indicate that the method of the present invention is useful for the detection of vital DNA sequences. Probes specific for any vital DNA target of interest can be generated, RecA-protein coated, and used in the in situ hybridization method of the present invention. In addition to fluorescent detection a number of other detection methods might be used including, not limited to, the following: chemiluminescence (Tropix Inc., Bedford, Mass.) and radioactivity.

The method of the present invention also has a good specificity of target detection. The specificity of the present method was examined as follows. Thirty ng of RecA coated single-stranded biotinylated HBV probe was reacted with ATCC HCC "Alexander" cells using a standard native in suspension fluorescence in situ hybridization protocol (Example 10).

The specificity of the reaction signal for HBV targets was tested by adding 240 ng of either excess RecA-coated single-stranded non-biotinylated homologous DNA, or 240 ng of nonhomologous competitor DNAs (Example 10). Biotinylated HBV probe and non-biotinylated HBV and φx174 competitor DNAs were nick-translated under the same conditions to insure that they were of a similar size (average 400–500 bs). Unlabeled human placenta DNA, (100–120 bp fragments) was obtained from Oncor ("BLOCKIT™ DNA"). The results (Table 1; Example 10) show that only homologous HBV DNA, not heterologous DNAs, specifically competes with the biotinylated HBV DNA probe signal.

Representative cells from the competition experiments described in Table 1 are shown in FIG. 16. In the FIG.: 16A, Biotinylated HBV probe+excess unlabeled HBV DNA; 16B, Biotinylated HBV probe+excess unlabeled φx174 DNA; and 16C, Biotinylated HBV probe+excess unlabeled human placenta DNA. FITC probe signals were observed with a Zeiss LSM in laser scanning mode. The observed FITC signals from the HBV probes are shown superimposed on the phase images of the cells. Note that it is clear from the signal and cell images that homologous HBV DNA specifically competes with the biotinylated HBV DNA probe signal but heterologous DNA does not compete. Thus, the RecA-facilitated native fluorescence in situ hybridization reaction detects specific nucleic acid targets that are homologous to labeled probe DNA.

From the foregoing, it will be appreciated how various objects and features of the invention are met. The invention provides a simplified and less time consuming procedure(s) for localizing target sequence in a biological structure. The method reduces artifacts by eliminating the need for a heat denaturation step and by reducing the need for signal enhancement, and allows more rapid and well defined detection of target sequences, including target sequences of low copy number.

In particular, the method allows detection of low-copy sequences without the requirement to first amplify the sequences. A comparison of FIGS. 2A and 2B demonstrate that this feature greatly enhances the specificity and resolution of the method over prior art approaches. Since most gene mapping and chromosomal studies are expected to involve specific low-copy sequences, the present method provides an important advantage for diagnostic gene mapping studies, as well as for diagnostic application involving unique or low-copy numbers of various pathogen sequences. These later applications are described in Section II below.

Further, the methods described herein are efficacious for the detection of (i) unique, i.e., single copy, gene sequences, and (ii) unique or multiple viral nucleic acid sequences, in hybridization reactions carried out in solution and on slides.

As disclosed in the co-owned patent application for "Diagnostic Applications of Double D-Loop Formation" filed on even date herewith, stable RecA-coated probes prepared from duplex DNA fragments can form double-probe hybrid structures with target duplex DNA. Although such double-probe structures have not been shown for probe binding under in situ hybridization conditions, the presence of such structures, if formed, could be exploited to effectively double the amount of signal produced at the in situ target site. Further, the two probes could be labeled with different reporter groups, for example, fluorescent probes with different absorption or emission peaks, so that target sites containing both probes could be distinguished from sites containing one probe only.

II. Applications

One general application of the invention is for diagnostic use in locating and visualizing a selected gene or regulatory sequence in a chromosome, and/or in a particular region of the chromosome. The target gene or sequence may be one which (a) generates a selected gene product, (b) is suspected of performing a critical cell-control function, such as that of a ribosome, an oncogene, or a tumor suppressor gene, (c) is related to a repeat sequence, (d) is suspected of containing a genetic defect which prevents expression of an active gene product, (e) may be related in chromosome position to a marker probe region with a known map position, and/or (f) may represent an integrated or non-integrated viral sequence, such as a DNA-hepatitis virus (e.g., Hepatitis B Virus (HBV) (Ono, et al.; Fujiyama, et al.; Galibert, et al.) in fixed chromatin or fixed virions.

The diagnostic probe used in the method may be obtained, in some cases, from available plasmids, cosmids, viruses or other vectors, such as from human genomic libraries or may be chemically synthesized. Where the gene product is available, the probe may be generated by sequencing enough of the protein product to generate probes for PCR amplification, and amplifying and tagging the corresponding gene sequence in genomic DNA using the probes in a PCR format. The amplified gene material can be purified by electrophoresis and used directly as the probe, or cloned into suitable vectors, using standard protocols.

In a typical method, the nuclei are derived from cells staged in metaphase, using well known methods, then fixed and "dropped" on a glass slide to produce a metaphase chromosomal spread. Alternatively, the chromosome material under investigation may be a spread of an isolated individual chromosome(s).

FIG. 4A shows a single metaphase chromosome 10 which may be in isolated form or part of a field containing an entire set of somatic-cell chromosomes. The chromosome contains a known marker region 12 (gene site M) whose map location on the chromosome is known, and is suspected of containing a gene region of interest. The chromosome preparation on a slide is reacted with the probe complex, indicated at 14 in FIG. 4A, and composed of a probe 16 coated with RecA protein, shown by circles at 18, and having biotin groups, indicated by vertical dashes at 26. Reaction of the probe complex with the chromosome material, in accordance with the invention, leads to homologous binding of the probe to a gene site S (FIG. 4B) which is the target region of interest.

The binding site S may be visualized, for site localization by a variety of methods. In one method, illustrated in FIG. 4C, a second probe complex 22 composed of a probe 24 homologous to known region 12 (gene site M) and also containing biotin groups 26 is added to the chromosome preparation, and allowed to bind to its region of homology. After washing to remove unbound probe, the preparation is reacted with an FITC-avidin reporter 28, to label both sites on the chromosome with a fluorescent tag.

When viewed by fluorescence microscopy, a field such as shown at FIG. 4C is seen, with the two fluorescence points, shown at 30 in FIG. 4C, providing an indication of the distance between the marker and test sequences on the chromosomes.

In another visualization method, shown in FIG. 4D, the chromosomes are labeled with one or more specific fluorescent dyes, indicated at 32, which give characteristic staining patterns in metaphase chromosomes (Korenberg, Lawrence, 1990). The chromosomes are also labeled with an avidin reporter 34 containing a fluorescent label having a different fluorescence excitation wavelength from that of the band staining fluorescent molecule(s). Using fluorescence microscopy, the chromosomes are visualized at one wavelength, as indicated at 36 in FIG. 4D, and the location of the probe on the chromosomes site is visualized at a second excitation wavelength. Although reaction with one homologue is shown (4D) all homologous sequences would react with probe.

The invention also provides an improved-method for detecting a variety of chromosomal abnormalities.

Figure 5A:
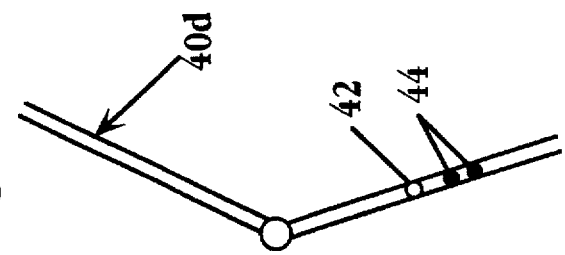
Figure 5B:
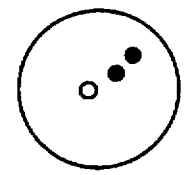

FIGS. 5–10 illustrate how the method can be applied to detecting various types of chromosome aberrations. FIG. 5, frame A shows a normal chromosome 40a containing two linked marker regions 42 and 44 on one of the chromosome arms. The two regions in the chromosome are hybridized with individual probe complexes, in accordance with the invention, then labeled with different fluorescent tags. For example, one of the regions may be labeled with an avidin-linked fluorescence reporter specific against biotin groups on one probe complex, and the second region, labeled with a second fluorescence reporter carried on an anti-digoxigenin antibody specific against digoxigenin groups on the second probe complex. The first and second fluorescence reporters are indicated by open and solid circles, respectively in FIG. 5 and in related FIGS. 6–10.

When the two regions are examined by fluorescence microscopy, at the appropriate excitation wavelengths, the two regions are localized by two distinguishable fluorescence spots (indicated by open and solid circles, in frame B). The two spots indicate the relative orientation of and distance between the two genomic regions in the normal chromosome.

Figure 6A:
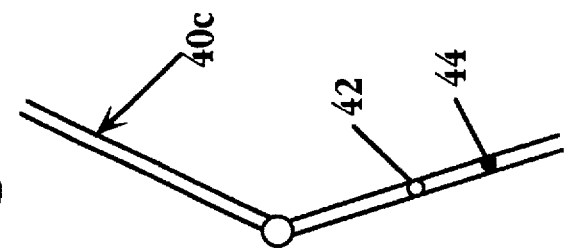
Figure 6B:
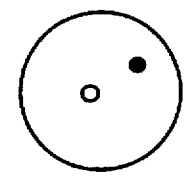

FIG. 6 illustrates, in frame A, a chromosome 40b which differs from chromosome 40a by a deletion of chromosome region 44. The mutation is seen, in frame B, as a single fluorescence spot at an excitation wavelength corresponding to region 42 only.

Figure 7A:
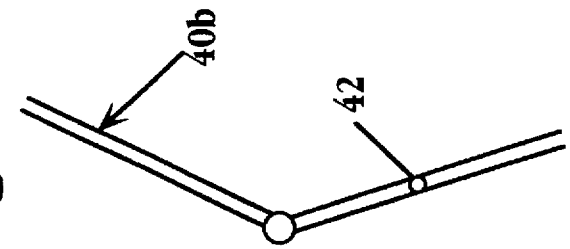
Figure 7B:
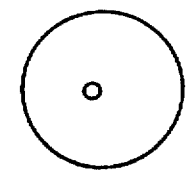

FIG. 7 illustrates, in frame A, a chromosome 40c which differs from chromosome 40a by an insertion between regions 42, 44 in the chromosome. The insertion is evidenced, in the fluorescence microscopy field seen in frame B, by a greater distance between the two fluorescence spots with respect to the FIG. 5 distance.

Figure 8A:
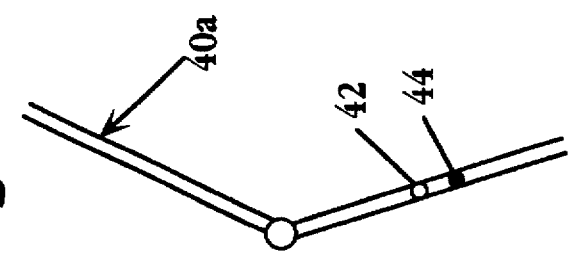
Figure 8B:
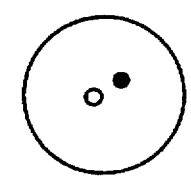

FIG. 8 illustrates, in frame A, a chromosome 40d which differs from chromosome 40a by a duplication of the region 44. The duplication is seen, in Frame B, as a doublet at the excitation wavelength of the region 44 probe, as indicated.

FIG. 9 illustrates, in Frame A, a chromosome 40e which differs from chromosome 40a in that a segment containing region 44 has translocated to a second chromosome 48e. The translocation is evidenced, in Frame B, by widely spaced fluorescence spots. The identity of chromosome 48e may be determined, as above, by staining the chromosomes with dyes which form characteristic metaphase banding patterns (or using chromosome 48 marker hybridization), as above.

FIG. 10 shows, in frame A, a chromosome 40f which differs from chromosome 40a in that the segment carrying regions 42, 44 has been inverted. The inversion is evidenced, in Frame B, by reversal of positions of the two fluorescence spots.

FIG. 12 shows the ability of the method of the present invention to detect specific chromosomal DNA sequences in metaphase chromosomes using native RecA-mediated fluorescence in situ hybridization. These data support the use of the method of the present invention for native fluorescence in situ hybridization on slides. Example 6 describes the steps used to generate the metaphase chromosome fluorescence in situ hybridization signals represented in FIG. 12 including the following: the preparation of chromosome 1 alpha-satellite probe and HEp-2 cells pretreated with acetate buffer at 60° C. As expected, in FIG. 12, the FITC hybridization signal is located at the centromere. These data support that the native RecA-mediated fluorescence in situ hybridization technique can be used to visualize sequence and gene position on nondenatured DNA in fixed chromosomes or chromatin.

FIGS. 13 and 14 show the ability of RecA-mediated native fluorescence in situ hybridization detection of tumor suppressor gene sequences. The native RecA-mediated fluorescence in situ hybridization technique can be used to detect and visualize a unique single copy gene sequence in fixed cells in suspension (FIGS. 13A to 13F) and on slides (FIGS. 14A to 14D) without any signal amplification steps. The results show the detection of unique p53 sequences on chromosome 17 in ATCC HEp-2 and HCC "Alexander" cells (Examples 7 and 8).

FIG. 15 illustrates the ability of RecA-mediated native fluorescence in situ hybridization to detect nucleic acid sequences in ATCC HCC "Alexander" cells in suspension. FIG. 15 (Example 9) shows hybridization signals obtained using two different biotinylated HBV probes, "BIO-PROBE®" (FIG. 15A to 15B) and pAM6 (FIG. 15C to 15E). Viral targets were detected in ATCC HCC "Alexander" cells, known to contain HBV nucleic acid sequences, probed using The native fluorescence in situ hybridization technique in cell suspension. HEp-2 cells, not infected with HBV nucleic acid sequences and probed with the same probes and techniques, did not show any hybridization signals. These results support the use of the method of the present invention to detect diagnostically important viral target sequences in HBV-infected human liver cells.

Figure 16A:
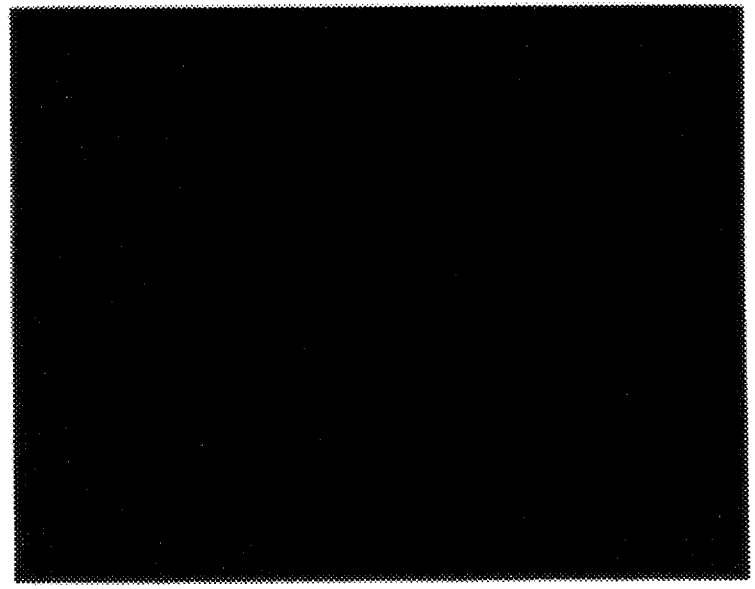
FIGS. 16A to 16C show specificity of HBV target detection using RecA-mediated native fluorescence in situ hybridization detection in human HCC cells tested by competition hybridization.
Figure 16B:
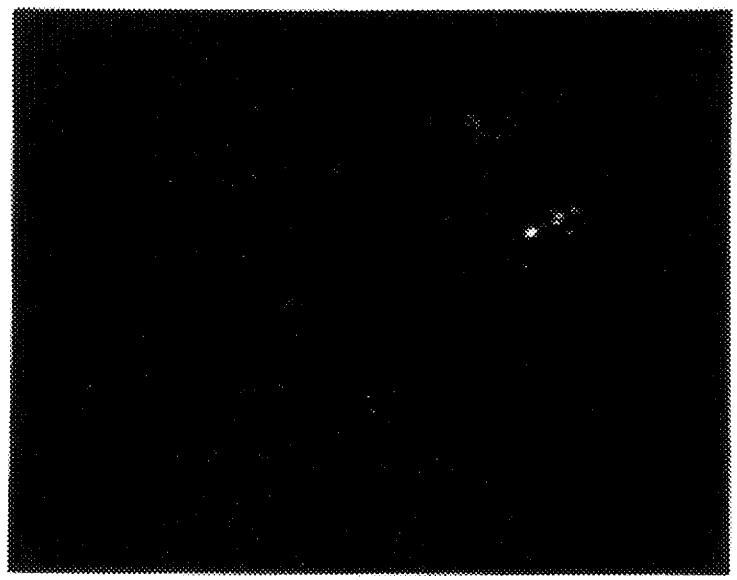
Figure 16C:
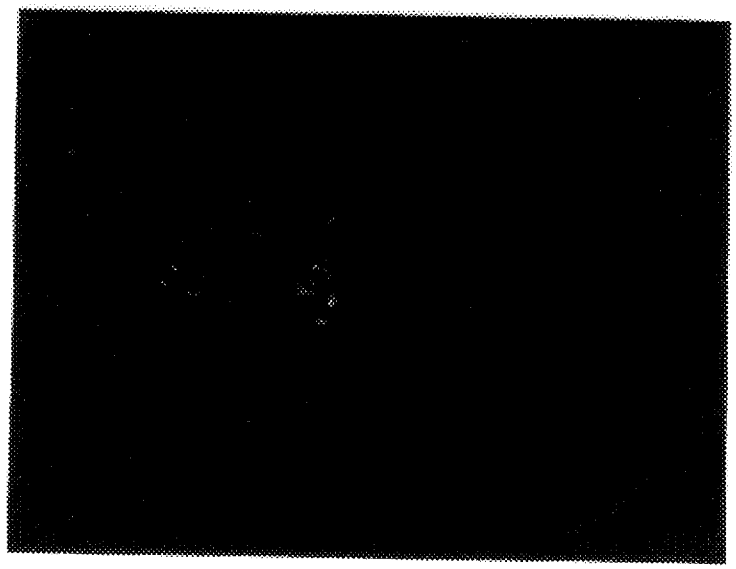

FIG. 16 demonstrates the specificity of HBV target detection using native fluorescence in situ hybridization. The native fluorescence in situ hybridization assay specifically identifies nucleic acid targets homologous to probe DNA (FIG. 16 and Table 1). This was demonstrated by showing that biotinylated pAM6 HBV DNA probe hybridization signal is specifically competed when reactions contain excess homologous unlabeled pAM6 DNA (FIG. 16A) but not when they contain either excess nonhomologous unlabeled $\phi$×174 DNA (FIG. 16B) or excess unlabeled human placenta DNA (FIG. 16C). The results of these competition experiments demonstrate that native RecA-mediated fluorescence in situ hybridization signals, e.g., with HBV probe DNA and HCC cells in suspension, are HBV specific.

Generally, the RecA-mediated fluorescence in situ hybridization reactions of the present invention use RecA protein, cofactor, and 1-2 hour incubation times. Single-stranded probes in a broad size range work, including, but not limited to, average sizes of 100-200, 200-400, 300-500, 400-600, and up. Typically, size ranges above 100-200 are preferred and 300-500 are most preferred. Probes coated with RecA protein can be stored in the freezer for future use: probes stored for up to 7 days have been tested and gave good hybridization signals.

The above described competition experiments have demonstrated that the RecA-mediated native fluorescence in situ hybridization is specific for detecting homologous nucleic acid sequences. The hybridization reaction is capable of detecting single copy genes and sequences (e.g., p53), multiple copy sequences (e.g., alpha-satellite chromosome 1), and diagnostically important viral target sequences (e.g., HBV). Native RecA-protein mediated fluorescence in situ hybridization reactions are in general, more rapid than standard denatured fluorescence in situ hybridization assays. Experiments performed in support of the present invention indicate that washing in 1.75×SSC after hybridization improves signal and decreases background.

Some features of the present invention for native RecA-mediated fluorescence in situ hybridization include the following: native RecA-mediated fluorescence in situ hybridization can be used on 1× PBS washed, 100% methanol fixed (or 70% ethanol fixed) cells in suspension; signals can be achieved with two hours, or less, of incubation with probe; the reaction is efficient—for example, with 50 ng probe and standard conditions, the reaction averages between 65-90% of cells with signal, depending upon the concentration of probe used; the reaction works with less than 50 ng probe—concentrations of probe in excess of 10 ng are preferred; a number of cofactors, including ATPγS, GTPγS, ATP, dATP and a combination of ATPγS and ADP, work in these reactions—one embodiment employs ATPγS concentrations in the range of approximately 0.24 to approximately 2.4 mM (preferred embodiments include the range of approximately 0.24 to 0.48 mM); a wide range of RecA monomer:nucleotide ratios work well, including 1:1, 1:0.8, 1:2 and 1:2.5 (a preferred embodiment utilizes 1:2); the amount of signal obtained with a Chromosome #1 alpha-satellite probe and native RecA-mediated fluorescence in situ hybridization on slides with HEp-2 cells are comparable to those obtained using a standard denatured fluorescence in situ hybridization technique; the reaction works in the presence of accessory proteins (e.g., single-strand binding protein (SSB), topoisomerase I and topoisomerase II); and when the reactions are carried out for samples fixed on slides the reaction efficiency is improved from an average range of 5-20% to 55-80%, by incubating slides in 10 mM Tris-acetate buffer pH7.5 at 55°-60° C. for 30-45 min before adding RecA-coated probe mix. This temperature is below the denaturation temperature of intracellular nucleic acids.

It will be appreciated that the above applications of the method, to the extent they involve probe binding to a single or small-copy-number target sequence are uniquely suited to study by the present method.

Another general application of the method of the invention is for diagnostics, typically for detecting changes in chromosome ploidy or rearrangement, or presence of a viral or bacterial or parasitic pathogen in an infected organism, organ, tissue, or cell. This application is specifically discussed above and is generally illustrated in FIGS. 11A–11C for detection of virus infected cells, such as cell 50. Virion particles (or integrated viral genomes) contained in the cell are shown at 54. The cells, e.g., blood cells, are obtained from the test subject, and treated to permeabilize the cellular structures, as discussed above. To the permeabilized cells (FIG. 11A) is added a virus-specific DNA probe complex 56, with sequence specific binding of the DNA complex to virus duplex nucleic acid being followed by addition of a fluorescent marker molecule 58, for virus-complex labeling (FIG. 11B). The probe signal may be enhanced, if necessary, by the amplification of reporter reagents described above, e.g., a biotinylated anti-avidin antibody, followed by a second fluorescence-labeled avidin reporter molecule.

The labeled cells may be examined by fluorescence microscopy, to detect and localize infecting virus nucleic acid in the cells. Alternatively, cell infection, and percent cells infected, can be determined by fluorescence activated cell sorting (FACS), as illustrated in FIG. 11C. This figure shows a group of blood cells, such as cells 60, 62 passing through a capillary tube 64 in a FACS device equipped with a detector 66 for detecting fluorescence in individual cells passing through the detector region. Fluorescence labeled cells are indicated by dark shading in the figure. It is seen that the method provides rapid detection of infected cells, for diagnostic purposes, and is capable of measuring level of infection and percentage of cells infected. Thus, for example, the method can be used to assess the progress of an anti-virus treatment, by measuring decreases in cell infection over the treatment period.

The FACS device may be further equipped with sorting apparatus for capturing fluorescence-labeled cells, to form a concentrate of infected cells. The concentrate, in turn, can be used as a source of viral nucleic acid, for purposes of identifying and cloning the viral genome.

The following examples, which are intended to illustrate but not limit the invention, illustrate particular methods and applications of the invention.

EXAMPLE 1

Purification of RecA Proteins

RecA and RecA803 proteins were isolated from the overproducing strains JC12772 and JC15369 (obtained from A. J. Clark and M. Madiraju), or RecA was purchased from Pharmacia.

RecA and RecA803 proteins were purified by modification of published procedures (Shibata, Griffith) involving fast protein liquid chromatography (FPLC) using a hydroxylapatite column (obtained as powder from BioRad) followed by an anion ("MONO®Q", Pharmacia) exchange column.

Protein purification was monitored as follows:

(i) identifying the 38,000-dalton RecA protein by SDS-PAGE ("PHASTGEL™" system, Pharmacia, Piscataway N.J.);

(ii) assay of the RecA ssDNA-dependent ATPase activity using [γ-$^{32}$P]ATP and single-stranded DNA (Shibata). The products of the reaction were separated using PEI cellulose thin-layer chromatography Science, NJ): the PEI plates were developed in a solvent of 0.5M LiCl and 0.25M formic acid. Products were detected by autoradiography.

(iii) assay of DNase activity. DNase activity was monitored by incubating the RecA protein samples with a mixture of φx174 linearized and supercoiled circular double-stranded RF and circular single-stranded DNAs in RecA strand-transfer buffer (Cheng) for 1 hr at 37° C. DNA nicking and digestion were monitored after deproteinization by visualizing the DNAs with ethidium bromide after agarose gel electrophoresis and comparing the quantities of each DNA type in the RecA incubated samples with those incubated in buffer without RecA. Only RecA protein samples showing no detectable DNase activity were used.

(iv) assay of D-loop activity with 500-mer oligonucleotide probe using a method modified from Cheng.

Silver stained SDS-polyacrylamide gel profiles of the final "MOMONO-Q®"-purified RecA and RecA803 proteins showed a single 38,000-dalton from each preparation that was essentially free of other cellular polypeptides.

EXAMPLE 2

Preparation of Probe Complex

Biotinylated chromosome X alpha satellite DNA probe was obtained from ONCOR (Gaithersburg, Md.).

Probe diluted in sterile MilliQ® (Millipore) $H_2O$ was denatured in a 0.5 ml microcentrifuge tube in a 100° C. heat block for 5 min, and the tube immediately placed in an ice water bath. Approximately 5 min prior to addition of denatured probe to the hybridization mixture the tube containing the probe was placed in ice in a freezer at −20° C. The probe hybridization mixture contains the following components in a broad range of concentrations and is combined in the order listed: 1 µl of 10× RecA reaction buffer [10× RecA reaction buffer:100 mM Tris acetate pH 7.5 at 37° C., 20 mM magnesium acetate, 500 mM sodium acetate, 10 mM DTT and 50% glycerol (Cheng)); 1.5 µl ATPγS from 16.2 mM stock (3.24 and 1.62 mM stocks can also be used), (Pharmacia) (rATP, daTP, GTPγS, or a combination of ATPγS and ADP may be used in some reactions); 0.75 µl 20 mM magnesium acetate; 4–60 ng (or more in some reactions) of denatured probe in sterile ddH$_2$O or TE (20 mM Tris HCl, pH7.5, and 0.1 mM EDTA); RecA (when prepared in our own laboratory and the exact amount of µl added varies depending on concentration of stock, when purchased from Pharmacia, 1.25 µl 0.137 mM stock). The mixture was incubated at 37° C. for 10 min followed by addition of 0.5 µl/reaction of 200 mM magnesium acetate. Final concentrations of reaction components are: 4.0 mM to 10 mM Tris acetate, 2.0 mM to 15 mM magnesium acetate, 20.0 mM to 50 mM sodium acetate, 0.4 mM to 1.0 mM DTT, 2% to 5% glycerol, 0.24 mM to 2.5 mM ATPγS, 0.005 mM to 0.02 mM RecA.

EXAMPLE 3

In situ Hybridization with Chromosome X Probe

A. Preparation of HEp-2 Cell Nuclei

HEp-2 cells were originally derived from human male larynx epidermoid carcinoma tissue. HEp-2 is chromosome ploidy variable (Chen).

The cells were cultured for 24 hours after seeding in DMEM (Whittaker or GIBCO-BRL) supplemented with 10% FBS, sodium pyruvate and Penstrep antibiotics mix at 37° C. under standard conditions. The cells were pelleted by low-speed centrifugation and gradually resuspended in 75 mM KCl in a 37° C. water bath, and allowed to incubate for between 5 and 15 min for the desired amount of nuclear swelling to occur, followed by addition of 3:1 ice cold methanol:acetic acid and centrifugation at 6° C.

One ml of fluid was left in the tube with the pelleted cells, additional ice cold methanol:acetic acid was added, and the cells suspended by gentle mixing of the tube, followed by centrifugation. Repeated additions of methanol:acetic acid degrades cytoplasm and isolated nuclei were obtained by repeated additions of methanol:acetic acid followed by mixing and centrifugation as above. (HEp-2 and other cell types may be fixed in alternative ways, some of which do not degrade fixed cytoplasmic structures).

Finally, the preparation of nuclei was resuspended in 3:1 methanol:acetic acid at a concentration about 2×10$^6$/ml and is either dropped by pipette in 10 µl aliquots onto clean glass slides which were stored at −20° C., or the suspended nuclei or cell preparation are stored at −20° C. for later use.

B. Nondenatured Nucleic Acid Target-Hybridization Reaction

Ten µl of probe mixture/reaction from Example 2 was applied to the fixed preparation on glass slides. Glass coverslips were placed over the hybridization areas and sealed with rubber cement, and reactions were incubated enclosed in a moist container in a 37° C. $CO_2$ incubator for between 1–4 hours. Following incubation, the rubber cement was removed and the slides were washed in coplin jars 3 times for 10 min each in 2×SSC (20×SSC: 3M NaCl, 0.3M sodium citrate, pH 7.0 is used in all SSC containing preparations in these assays) in a water bath at 37° C. Other wash conditions may also be used.

The slides were placed in preblock solution [4×SSC, 0.1% Triton®X-100, 5% Carnation®nonfat dry milk, 2% normal goat serum (Gibco), 0.02% sodium azide, pH 7.0] for 25 min at room temperature (RT), followed by immersion in 5 µg/ml FITC-avidin DCS, cell sorter grade (vector, A-2011) in preblock solution for 25 min at RT. The slides were washed in 4×SSC, 4×SSC and 0.1% Triton® X-100, and 4×SSC for 10 min each at RT, followed by brief rinsing in double-distilled H$_2$O and dried. Antifade was applied [100 mg p-phenylenediamine dihydrochloride (Sigma P1519) in 10 ml PBS adjusted to pH g with 0.5M carbonate-bicarbonate buffer (0.42 g NaHCO$_3$ adjusted to pH 9 with NaOH in 10 ml ddH$_2$O) added to 90 ml glycerol, and 0.22 um filtered], and antifade mounting medium and coverslips were placed over the preparations. Antifade containing a counterstain such as propidium iodide or DAPI was sometimes used instead of antifade alone. FIG. 1A shows a fluorescence micrograph of a cell nucleus from the above preparation (no signal amplification).

If necessary, signal amplification may be performed as follows: Slides are washed for 5–10 min in 4×SSC and 0.1% Triton X-100 at RT to remove coverslips and antifade, followed by incubation in preblock solution for up to 20 min, then are incubated with biotinylated goat anti-avidin antibody (Vector BA-0300) a: a concentration of 5 µg/ml diluted in preblock solution for 30 mix at 37° C. Slides are washed for 10 min each in 4×SSC, 4×SSC and 0.1% Triton®X-100, 4×SSC at RT followed by incubation in preblock solution for 20 min at RT, then immersed in preblock solution with 5 µg/ml FITC-avidin for 20 min at RT. Slides are again washed in the 4×SSC series, briefly rinsed in dd H$_2$O, and mounted with antifade or antifade with counterstain.

C. Hybridization by Heat Denaturation of the Nucleic Acid Target

For comparative purposes, in situ hybridization by heat denaturation of nuclear substrate was performed in parallel. Denatured labeled X chromosome probe was added to the nuclei, denatured on a slide under ONCOR protocols. The same nuclear preparations were used as in the nondenatured method. The signal amplification procedure suggested by ONCOR was used to enhance the hybridization signal. Thereafter, the slide was maintained at 37° C. overnight. The procedures and materials generally followed that of the ONCOR®Chromosome In situ Kit, Cat No. S1370.

FIG. 1B shows a fluorescence micrograph of a cell nucleus from the above signal amplified preparation.

EXAMPLE 4

In situ Hybridization with Chromosome 7 Probe

Biotinylated DNA probe to chromosome 7 alpha satellite DNA was obtained from ONCOR. The probe was denatured and could be stored frozen for at least five weeks. 32 ng of denatured freshly thawed DNA probe in 16 µl (1:2, probe:H$_2$O, 2 ng/µl DNA) were added to the same amount of hybridization mixture and in the same order given in Example 2. Following incubation of the probe mixture at 37° C. for 10 min and final addition of 0.5 µl 200 mM magnesium acetate, the reaction contained a total of 21 µl.

Probe was incubated on the nondenatured HEp-2 target cell nuclei (Example 3B) for 2.5 hours at 37° C. in a incubator followed by washing, blocking, and FITC-avidin incubation exactly as described for probe to chromosome X in Example 3B. The time to conduct the experiment, including the ethanol series treatment of the slide was approximately 5 hours. FIG. 2A shows a fluorescence micrograph of a cell nucleus from the treated preparation.

For comparison, the nuclei were reacted with chromosome 7 probe under heat-denaturation conditions, as in Example 3C. Briefly, 5 ng denatured probe chromosome 7 alpha satellite DNA was combined with hybridization buffer (Hybrisol®V1, ONCOR, as in FIG. 1B) and denatured using ONCOR protocols. 7 µl of the probe mixture was hybridized with HEp-2 cell nuclei for 16 hours and the reaction treated according to ONCOR protocols, including signal amplification. FIG. 2B shows a fluorescence photomicrograph of the treated denatured nuclei.

EXAMPLE 5

Detection of Specific Chromosome Sequences in Methanol Fixed Interphase Nuclei in Suspension A probe specific for the X chromosome alpha satellite DNA, Oncor probe stock (also used in Example 2) was diluted and denatured at 100° C. for 5 min, immediately placed in an ice-water bath (for approximately 15 min) and stored in a −20° C. freezer briefly (about 5 min) before addition to the hybridization mixture. The hybridization mixture was combined in the following order (components, concentrations, and mixtures are described in detail in Example 2): 1 µl 10× RecA reaction buffer (see Example 2), 1.5 µl ATPγS (16.2 mM stock, Pharmacia), 0.75 µl magnesium acetate (20 mM stock), 12 µl of denatured probe (ONCOR) containing 60 ng in a 1:2 dilution in H$_2$O (20 ng or more than 60 ng can also be used), RecA (0.137 mM stock, Pharmacia). The mixture was incubated in a 37° C. water bath for 10 min followed by addition of 0.5 µl 200 mM magnesium acetate.

HEp-2 cells were fixed in 100% methanol-(or other appropriate solutions) at −20° C. at a concentration of approximately 2.5×10$^6$/ml. About 0.5 ml of the suspended cells (1.25×10$^6$) were centrifuged in a "TOMY" centrifuge set at 6° C. in a 1.5 ml microcentrifuge tube and resuspended followed by centrifugation in 200 µl to 1 ml of 70%, 85% and 100% ice cold EtOH. After the final centrifugation and removal of 100% EtOH supernatant the pellet was resuspended in 200–500 µl 1× RecA reaction buffer at RT, and placed in a 0.5 ml centrifuge tube and centrifuged.

The completed probe mixture was mixed with the pellet, and the tube placed in a 37° C. water bath for 1.5–2.5 hours. Incubation was stopped by addition of 250 µl 2×SSC (prewarmed to 37° C.) followed by centrifugation. The pellet was resuspended in 2×SSC (prewarmed to 37° C.) and incubated for 5 min at 37° C. Following centrifugation the pellet was resuspended in 500 µl blocking solution at RT for 20 min, then centrifuged and resuspended in 10 µg/ml FITC-avidin in 100 µl blocking solution at RT in the dark, for 20 min. The tube was centrifuged and 250 µl 4×SSC mixed with the pellet, again centrifuged, and 250 µl 4×SSC with 0.1% Triton®X-100 mixed with the pellet and again centrifuged with 250 µl 4×SSC all at room temperature. After a final centrifugation the pellet was mixed with approximately 20 µl antifade. Specific signal was noted in approximately 30% of the suspended cells. Note: Experiments using 100% methanol fixed whole cells and/or fixed nuclei and other concentrations of different washing components have shown 50–90% reaction.

The FIG. 3A photomicrograph shows a dividing fixed HEp-2 cell nucleus, as viewed with a Zeiss LSM-10 microscope, illustrating the symmetrically located FITC-labeled probe-bound centromeric targets. The phase picture in FIG. 3B below was taken of the same nucleus without changing the microscope focus.

EXAMPLE 6

Detection of Specific Chromosomal DNA Sequences in Metaphase Chromosomes

Biotinylated probe to chromosome 1 alpha-satellite centromeric sequences (pUC1.77: a 1.77 Kbase pair long human EcoRI fragment in the DNA vector pUC9; Cooke, et al.; Emmerich, et al.) was prepared using the BRL Nick-translation System in the presence of bio-14-dATP (Gibco-BRL, Gaithersburg Md.). The nick translations were performed essentially as described by the manufacturer (BRL) with the following modification: twice the recommended amount of enzyme was added and the reaction was incubated at 15° C. for 1 hr 45 minutes. These nick translation reaction resulted in probes with an average single-strand size of approximately 300-400 bp.

Nick-translated probes were precipitated in 0.3M sodium acetate in ethanol, resuspended in 10 mM Tris-HCl pH 7.5, 0.1 mM EDTA, and the DNA concentration was determined with the "DNA DIPSTICK™"(Invitrogen). Methanol:acetic acid fixed HEp-2 cells (mostly nuclei; prepared similarly to Example 3) mounted on slides were dehydrated by exposure to a series of 70, 85, and 100% cold ethanol incubations. Dehydrated cells on slides were then preincubated in 10 mM Tris-acetate buffer, pH 7.5, at 60° C. for 45 minutes while the RecA-coated chromosome 1 alpha-satellite centromeric sequence probe mix was prepared.

The 60° C. preincubation treatment does not denature target DNAs but it does improve the efficiency of native RecA-mediated fluorescence in situ hybridization reactions performed on fixed cells on slides (from 5-20% to 60-82% improved hybridization). The warmed slide was cooled to 37° C. on a 37° C. surface before prepared probe mix was added to the fixed cell nuclei preparation. Cells were covered with a coverslip and the reaction was sealed with rubber cement.

The DNA probe was heat denatured at 100° C. in 5.16 µl dd $H_2O$ for 5 minutes, quick-cooled in an ice-water bath, centrifuged at 4° C. a "TOMY®" microcentrifuge for 20 seconds to collect the liquid, and then immediately added to a mixture containing the other reaction components. Chromosome 1 probe was coated with RecA protein in a reaction mixture containing 1 µl of 10× acetate reaction buffer (Cheng et al, 1988), 1.5 µl of 16.2 mM ATPγS (Sigma), 0.75 µl of 20 mM Mg(OAc)$_2$, 0.59 µl of RecA (11.05 µg/µl), 1 µl of DNA probe (50 ng/µl). The total volume of reaction mix after probe addition was. 10 µl. The probe reaction mix was incubated at 37° C. for 10 minutes and then 0.5 µl of 0.2M Mg(OAc)$_2$ was added. Probe mix was then added to the buffer-treated cell nuclei on slides at 37° C. The reaction was covered with a coverslip, sealed with rubber cement and incubated in a moist chamber at 37° C. for 2 hr.

After cell incubation with probe, the rubber cement was removed and the slide was washed 3× in 1.75×SSC (pH7.4) at 37° C., each wash was 10 minutes. The slide was incubated in filtered preblock solution (100 µl) at room temperature for 20 minutes, then with 5 µg/ml FITC-Avidin (Vector, DCS grade) in filtered preblock at room temperature for 20 minutes in the dark.

Slides were washed at room temperature 1× in 4×SSC, 1× in 4×SSC+0.1% "TRITON®X-100", and then finally, 1× in 4×SSC. Slides were dipped into dd$H_2O$ briefly after the last wash and allowed to air dry. Before coverslip addition, antifade was added and the cells were observed with a Zeiss LSM.

FIG. 12 shows the hybridization signal from the fixed HEp-2 metaphase chromosomes with the RecA-coated, biotinylated, nick-translated probe to human chromosome 1 alpha-satellite centromeric sequences. Under these conditions, 73% of the cell interphase nuclei including chromosome spreads showed signals. The chromosome alpha satellite specifically hybridized with the chromosome 1 centromere.

EXAMPLE 7

RecA-Mediated Native Fluorescence In Situ Hybidization Detection of Unique p53 Chromosome 17 Tumor Suppressor Gene Sequences A. First Conditions: FIGS. 13A and 13B 1.25×10$^6$ 100% methanol fixed ATCC HEp-2 (ATCC; American Type Culture Collection, 12301 Parklawn Dr., Rockville Md. 20852) cells were placed in a microcentrifuge tube and put through an ethanol series of 70%, 85% and 100% (Lawrence, 1988 and 1990; Example 5). The cells were pelleted between fixation steps. After the 100% ethanol treatment step the cells were saved as a pellet until just before addition of the 1× acetate reaction buffer wash. All cell centrifugations between steps were for 30 seconds at 2.5K in a "TOMY" microcentrifuge.

While probe is incubating with RecA protein, the pelleted cells was washed in 1× acetate reaction buffer (Cheng et al, 1988). The cells are pelleted again and as much of the buffer wash as possible was removed before the addition of the RecA-coated probe reaction mix.

Probe was coated with RecA protein for 10 minutes at 37° C. in a mix containing 1 µl of 10× acetate reaction buffer, 0.75 µl of 0.02M Mg(OAc)$_2$, 1.5 µl of 1.62 mM ATPγS (Sigma), 0.59 µl of 11.02 µg/µl RecA, heat denatured probe [5 µl p53 probe (10 ng/µl; Oncor Inc., Gaithersburg Md.) and 1.16 µl dd$H_2O$]. Before probe addition to washed cell pellet, 0.5 µl of 0.2M Mg(OAc)$_2$ was added to the probe mix. Cells were mixed with probe and incubated for 3 hr 50 minutes at 37° C.

After incubation, cells were washed 3× in 1.75×SSC pH7.4 (250 µl washes), then incubated at room temperature for 20 minutes in filtered preblock, pelleted, and the preblock removed. This step was followed by incubation at room temperature for 20 minutes with 50 µl of filtered preblock containing 5.0 µg/ml FITC avidin. Cells were washed in 4×SSC, 4×SSC+0.1% "TRITON®X-100", 4×SSC, all pH7.4, (250 µl/wash).

A small amount (e.g., approximately 20 µl) of antifade was added to the final cell pellet and a portion of the cells were placed on a slide, covered with a coverslip, and observed using a Zeiss LSM. Under these general conditions, 65% or more of the cells show bright p53 hybridization signals (FIGS. 13A and 13B).

B. Second Conditions: FIGS. 13C and 13D

All cells and cell washes were identical to Example 7A. Probe was reacted with RecA as described above with the exception that the 0.02M Mg(OAc)$_2$ was omitted and 0.75 µl of dd$H_2O$ was added instead. Under these conditions, 40% of the cells had bright hybridization signals (FIGS. 13C and 13D).

C. Third Conditions: FIGS. 13E and 13F

All cell washes were identical to Example 7A. Probe was reacted as described above (Example 7A) with the exception that probe coating mix contained 1.5 µl 16.2 mM ATPγS, the reaction mix was incubated for 13 minutes at 37° C. before addition of 0.5 µl 0.2 mM Mg(OAc)$_2$, RecA-coated probe was added to 1.25×10$^6$ 100% methanol fixed ATCC HCC "Alexander" cells and reacted for 3 hr 20 minutes at 37° C. Cell washing after probe reaction was as described in Example 7A except that cells were reacted with 50 µl of filtered preblock containing 10.0 µg/ml FITC-Avidin. Under these conditions, 82% of the cells had bright hybridization signals (FIGS. 13E and 13F).

EXAMPLE 8

RecA-mediated Native Fluorescence In Situ Hybridization Detection of Unique P53 Gene Sequences in HEp-2 Cell Nuclei on Slides Methanol:acetic acid fixed ATCC HEp-2 cells on slides were reacted with RecA-coated p53 (Oncor) probe. Cells were washed and prepared for probe addition as described in Example 6 with the exception that the 45 minutes incubation with 10 mM acetate buffer pH 7.4 was omitted.

p53 probe DNA coating was done as described in Example 6 except that 1.5 µl of 3.24 mM ATPγS, 0.59 µl of 5.51 µg/µl RecA and 0.5 µl containing 2U topoisomerase II (United States Biochemicals Corp., Cleveland Ohio) were added, and half as much denatured probe was added [2.5 µl (25 ng probe) in 3.66 µl dd $H_2O$].

After probe coating with RecA protein, 0.5 µl 0.2M $Mg(OAc)_2$ was added and the probe mix was applied to nuclei on slides. Washing conditions after reaction with probe were as described for Example 6. Under these conditions, 20% of the nuclei had bright hybridization signals (FIGS. 14A to 14D). The number of interphase nuclei with hybridization signals in this experiment is less than observed in FIG. 12 (Example 6)—no buffer incubation step was included in this protocol.

EXAMPLE 9

RecA-Mediated Native Fluorescence in Situ Hybridization Detection of HBV Nucleic Acid Sequences in ATCC HCC "Alexander" Cells in Suspension $1 \times 10^6$ of 100% methanol fixed HCC cells/reaction are placed in 0.5 ml sterile microfuge tubes, centrifuged for 30 seconds at 2K rpm in a "TOMY®" microcentrifuge at 4° C., and the supernatant removed. 200 µl of ice-cold 70% EtOH is added, the treated cells are centrifuged at 4° C., the supernatant removed, the dehydration step repeated and the sample centrifuged as above using, sequentially, 85% and 100% iced-cold EtOH.

The cells are centrifuged and resuspended in 200 µl 1× acetate reaction buffer (same as standard RecA acetate reaction buffer except, minus the glycerol), centrifuged, and resuspended in same 1× acetate reaction buffer (minus glycerol). Immediately before the addition of the probe reaction mixture, the cells are incubated at 37° C. for 10 minutes, centrifuged at room temperature and the supernatant removed.

Biotin-labeled HBV-specific "BIOPROBE®" was obtained from Enzo Diagnostics, Inc. (New York N.Y.). This nick-translated probe is biotinylated with bio-11-dUTP, contains the whole HBV genome (adr4 serotype) and double-stranded probe fragments average 250 bp in size.

A second probe, pAM6, was obtained from the ATCC. pAM6 contains the whole HBV genome (adw serotype) in plasmid pBR322. pAM6 was labeled with bio-14-dATP by nick-translation with the BRL Nick-translation System as described in Example 6. Heat denatured single-stranded probe averaged 300–500 bases in size.

Both HBV probes were coated with RecA protein a 10 µl reaction containing 1 µl 10× acetate reaction buffer (Cheng, et al, 1988), 1.5 µl 3.24 mM ATPγS, 0.75 µl 20 mM $Mg(OAc)_2$, 0.53 µl 5.5 µg/µl RecA, and heat denatured probe [0.23 µl "BIOPROBE®" (60 ng/µl) was in 5.39 µl dd$H_2O$; 5 µl pAM6 probe (10 ng/µl) was in 1.22 µl dd$H_2O$]. Probe coating reactions were incubated at 37° C. for 10 minutes, then 0.5 µl of 0.2M $Mg(OAc)_2$ stock solution was added and the probe mixes are added to the prepared cell pellets.

The prepared probe mixes were individually added to separate cell samples and incubated at 37° C. in waterbath for 2 hours. The reaction was stopped by the addition of 250 µl 1.75×SSC (pH 7.4) at 37° C. Each sample was mixed, the cells pelleted and the supernatant removed. 250 µl of 1.75× SSC was added and the samples incubated at 37° C. for 5 minutes. This wash was then repeated. The cells were pelleted and to each sample 300 µl of filtered preblock was added. The samples were incubated at room temperature for 20 minutes. The cells were pelleted and the preblock removed.

To the samples 90 µl of 5 µg/ml FITC-Avidin in filtered preblock was added. The samples were incubated at room temperature in the dark for 20 minutes. The samples were then pelleted and the supernatant removed. To each sample 250 µl 4×SSC was added, the sample mixed gently, and the cells pelleted. The supernatant was removed and 250 µl 4×SSC+0.1% "TRITON®X-100" added. Pellet cells, remove supernatant, add 250 µl 4×SSC. The cells were pelleted, supernatant removed, the pellet air dried, and 20 µl of antifade added. The samples were then examined using a Zeiss LSM.

Figure 15A:
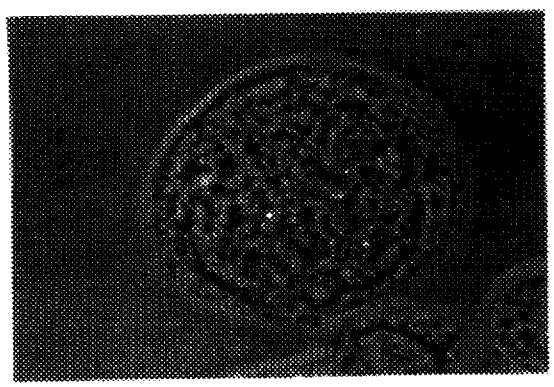
FIGS. 15A to 15E show RecA-mediated native fluorescence in situ hybridization detection of Hepatitis B Virus (HBV) nucleic acid sequences in ATCC HCC "Alexander" cells in suspension.
Figure 15B:
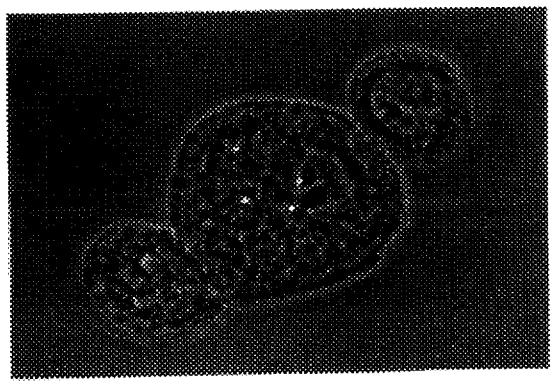
Figure 15C:
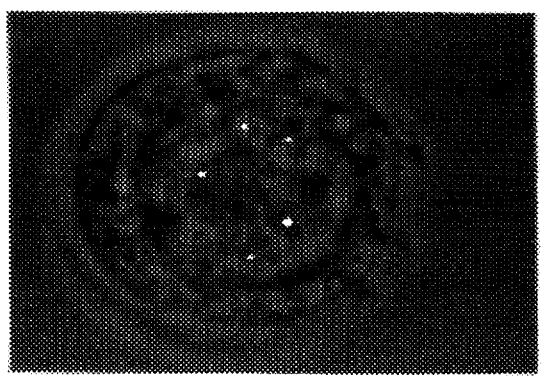
Figure 15D:
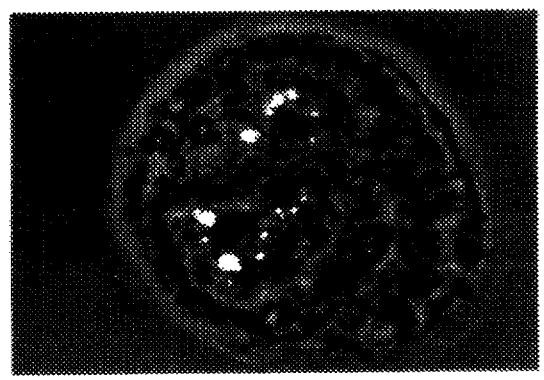
Figure 15E:
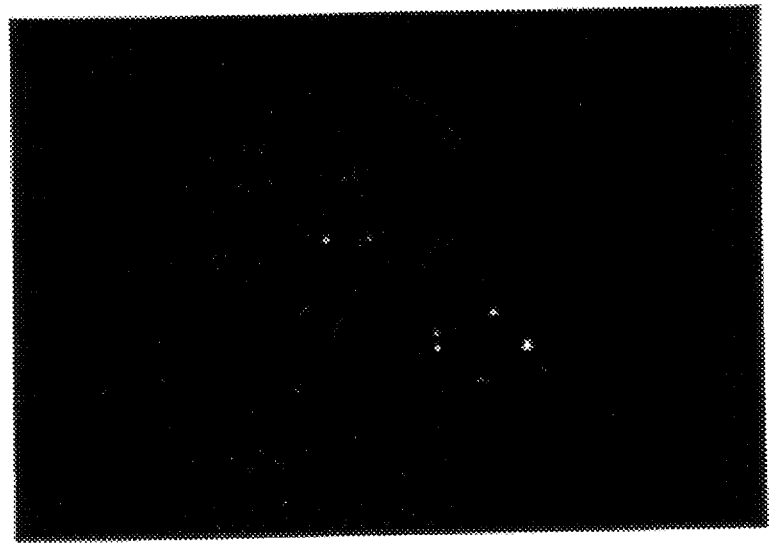

FIGS. 15A and 15B show the results of the above hybridizations using "BIOPROBE®": 81% of the cells had hybridization signals. FIGS. 15C to 15E show the results of the above hybridizations using the pAM6 probe: 95% of the cells had hybridization signals.

EXAMPLE 10

Specificity of HBV Target Detection Using Native Fluorescence In Situ Hybridization in Human HCC Cells Tested by Competition Hybridization A. Preparation of probes for competition assay Both biotinylated and unlabeled pAM6 (ATCC) and φx174 RFI (New England Biolabs) DNAs were prepared by nick-translation using the BRL Nick-translation System. Nick-translation was carried out essentially as described in Example 6, except that reactions for producing unlabeled DNAs contained dATP in place of bio-14-dATp.

Each competition reaction used $1 \times 10^6$ 100% methanol fixed cells and contained 30 ng of biotinylated pAM6 HBV probe DNA and 240 ng of competitor DNA. Biotinylated HBV probe DNA and unlabeled competitor DNAs were coated with RecA in separate reactions. After RecA coating, the $Mg^{++}$ ion concentration of each reaction was adjusted by adding 0.5 µl of 0.2 mM $Mg(OAc)_2$ per 10 µl of coating reaction. Then 10.5 µl of RecA-coated bio-pAM6 probe (30 ng of DNA) was mixed with an equal volume of RecA-coated competitor DNA (240 ng). The final volume of each mixture of RecA-coated biotinylated HBV probe and competitor DNA was 21 µl.

All biotinylated pAM6 DNA was coated with RecA and prepared for use in a single reaction, 10.5 µl of which was used for each competition experiment. Coating of all the biotinylated pAM6 probe in one reaction insured that there were no differences between reactions other than the DNA competitors. To allow proper RecA coating, both probe and competitor DNA coating reactions contained the same average RecA to nucleotide ratio (1 RecA protein monomer: 2 nucleotides).

All the biotinylated pAM6 probe was coated with RecA in a reaction containing 4 µl of 10× acetate reaction buffer (Cheng, et al, 1988), 6 µl of 3.24 mM ATPγS, 3 µl of 20 mM $Mg(OAc)_2$, 3.16 µl of 2.2 µg/µl RecA, and 12 µl of 10 ng/µl bio-pAM6 probe (which was heat denatured in 11.84 µl dd$H_2O$).

Each competitor RecA DNA probe coating mix contained 1 µl of 10× acetate reaction buffer, 1.5 µl 3.24 mM ATPγS, 0.75 µl 20 mM $Mg(OAc)_2$, 1.25 µl 11.05 µg/µl RecA, and either 4.8 µl of 50 ng/µl competitor DNA heat denatured in 0.7 µl ddH₂O (non-biotinylated φ×174 or non-biotinylated pAM6), or 2.4 µl of 100 ng/µl non-biotinylated placenta DNA ("BLOCKIT"; Oncor) heat denatured in 3.1 µl ddH₂O.

All probes were heat denatured at 100° C. for 5 minutes, cooled in ice-water approximately 20 sec, spun in a 4° C. microcentrifuge to collect all the liquid and immediately added to their respective RecA reaction mixture.

Probes were coated with RecA for 15 minutes at 37° C. and then 0.5 µl of 0.2M Mg(OAc)₂ was added/10 µl DNA mixture.

B. Reaction Mixtures

The −20° C. stored methanol-fixed cells were prepared for fluorescence in situ hybridization as previously described in Example 9 by dehydrating through a series of cold EtOH washes, followed by 2 times washes in 1× acetate reaction buffer (minus glycerol). Cells were incubated in the last wash buffer for 10 minutes at 37° C. before buffer was removed and the 21 µl of RecA-coated biotinylated probe and competitor DNA mixtures were added to the cell pellets.

Probes were reacted with cells in a 37° C. water bath for 3 hrs. Reactions were stopped by addition of 250 µl 1.75× SSC (pH 7.4) at 37° C., mixed, centrifuged at room temperature (RT) to pellet cells, and supernatant removed. Cells were washed twice with 250 µl 1.75×SSC at 37° C. for 5 minutes then spun down and the supernatant removed.

300 µl filtered preblock was added to treated, washed cells and incubated at RT for 20 minutes. After centrifugation and supernatant removal, 90 µl of 5 µg/ml FITC-Avidin in filtered preblock was added to each reaction, incubated at room temperature for 20 minutes in the dark. FITC-Avidin was removed after cells were pelleted by centrifugation. Reacted cells were washed consecutively in 4×SSC (pH 7.4) mixed gently with the cells, 250 µl 4×SSC+0.1% "TRITON®X-100" and 250 µl 4×SSC. After each wash, cells were pelleted and the wash liquid removed.

After the final wash, the cells were air dried and approximately 20 µl of antifade was added to each cell reaction. Cells were mounted on slides, covered with a coverslip and examined with the Zeiss LSM. Cells containing moderate to bright hybridization signal(s) were scored as positive for hybridization (see Table 1).

TABLE 1

Specificity of HBV fluorescence in situ hybridization in human HCC cells

| Competing DNAᵃ | # Cells with strong FITC FISH* Hybridization Signal | # Cells Counted | % Cells with strong FITC FISH Hybridization Signal |
|---|---|---|---|
| HBV | 0 | 154 | 0ᵇ |
| φX174 | 39 | 105 | 37.1 |
| Placenta | 30 | 99 | 30.3 |

ᵃNonbiotinylated.
ᵇ4.5% of these cells showed very faint FITC hybridization. Whereas FITC signals with the other competing DNAs were easily visible using the fluorescence microscope alone, the signals with this sample were only visible when 488 nm argon-ion laser illumination was used.
*fluorescence in situ hybridization.

The results presented in Table 1 show that only homologous HBV DNA, not heterologous DNAs, specifically competes with the biotinylated HBV DNA probe signal.

The cells shown in FIGS. 16A to 16C are from the competition experiments described in Table 1. In FIG. 16: 16A, Biotinylated HBV probe+excess unlabeled HBV probe DNA; 16B, Biotinylated HBV probe+excess unlabeled φ×174 DNA; 16C, Biotinylated HBV probe+excess unlabeled human placenta DNA ("BLOCKIT™" Oncor). FITC probe signals were observed with a Zeiss LSM in laser scanning mode.

The observed FITC signals from the HBV probes are shown superimposed on the phase images of the cells. Several cells from each experiment are shown. It is clear from the signal and cell images that homologous HBV DNA specifically competes with the biotinylated HBV DNA probe signal but heterologous DNA does not compete.

Although the invention has been described with respect to particular protocols and applications, it will be appreciated that a variety of changes and modifications may be made without departing from the invention.

It is claimed:

1. A method of identifying the presence of a known target sequence in a double-stranded nucleic acid contained in a fixed cellular or subcellular biological structure, in a defined morphological relationship with the structure, comprising adding to the structure, a probe complex composed of RecA protein stably bound to a single-stranded, reporter-labeled probe which is complementary to a duplex target sequence, under conditions in which the complex can contact the duplex nucleic acid target, allowing the complex to bind to the target sequence under non-denaturing conditions, removing unbound complex from said structure, and examining the structure for the presence of the reporter-labeled probe bound to the nucleic acid.

2. The method of claim 1, wherein the complex is stabilized by the presence of a cofactor selected from the group consisting of ATPγS, GTPγS, ATP, dATP and a combination of ATPγS and ADP.

3. The method of claim 1, wherein said probe is labeled with a ligand reporter, and said examining includes adding to the structure, specific ligand molecule, including antibodies, effective to stably bind to said ligand, and having a detectable reporter group.

4. The method of claim 1, for detecting the presence in a host cell, of a pathogenic (foreign) target duplex nucleic acid sequence, wherein said complex is added to the cells under conditions of host cell fixation, and said examining includes detecting the presence of a probe-bound reporter in said fixed cells.

5. The method of claim 1, wherein said examining includes detecting a fluorescent reporter bound to the reporter-labeled probe bound to the nucleic acid using either microscopy or a fluorescence activated cell sorter.

6. The method of claim 1, for localizing a selected target duplex nucleic acid sequence integrated into a host-cell genome, wherein said complex is added to the chromosomes of the cell, and said examining includes examining the chromosomes microscopically to determine the relative position of reporter-labeled probe in relation to chromosome ultrastructure.

7. The method of claim 6, wherein said chromosomes are labeled with one fluorescence reporter, said probe is labeled with a second fluorescence reporter, and said examining includes viewing the cells by fluorescence microscopy separately at wavelengths effective to excite fluorescence in each of the two reporters.

8. The method of claim 6, for localizing the target sequence in a selected chromosome, which further includes adding to the structure a second probe complex composed of RecA protein stably bound to a single-stranded, reporter-labeled nucleic acid probe which is complementary to a duplex strand in a known region of the selected chromosome, and said examining includes determining the relative positions of reporters associated with each of the two complexes.

9. The method of claim 8, wherein the first-mentioned complex and the second complex are labeled with different fluorescence reporters, and said examining includes viewing the cells by fluorescence microscopy separately at wavelengths effective to excite fluorescence in each of the two reporters.

10. The method of claim 1, which further includes amplifying the target duplex nucleic acid in the structure prior to said adding.

11. The method of claim 1, which further includes amplifying the probe bound to the target by addition of polymerase, and all four deoxytrinucleotides, where one of the deoxytrinucleotides includes a reporter label.

12. The method of claim 1, where said fixed structures are in solution or on a slide.

13. The method of claim 1, where said fixed structures are incubated in 10 mM Tris-acetate buffer, pH 7.5, at 55°–60° C. before the addition of said RecA probe complex.

14. The method of claim 1, where said allowing the complex to bind to the target sequence under non-denaturing conditions is carried out for less than 2 hours.

15. The method of claim 1, where said adding includes the addition of accessory proteins selected from the group consisting of toposiomerase I and topoisomerase II.

16. A method of identifying the presence of a known double-stranded viral nucleic acid target sequence contained in a fixed cellular or subcellular biological structure, comprising adding to the structure, a prone complex composed of RecA protein stably bound to a single-stranded, reporter-labeled probe which is complementary to the double-stranded viral nucleic acid target sequence, under conditions in which the complex can contact the double-stranded nucleic acid target, allowing the complex to bind the target sequence under non-denaturing conditions, removing unbound complex from said structure, and examining the structure for the presence of the reporter-labeled probe bound to the nucleic acid.

17. The method of claim 16, where the known viral target is a sequence derived from hepatitis B virus.

18. The method of claim 16, where the fixed structures are incubated in 10 mM Tris-acetate buffer, pH 7.5, at 55°–60° C. before the addition of the RecA probe complex.

19. The method of claim 16, wherein the complex is stabilized by the presence of a cofactor selected from the group consisting of ATP S, GTP S, ATP, dATP and a combination of ATP S and ADP.

20. The method of claim 16, wherein said probe is labeled with a ligand reporter, and said examining includes adding to the structure, specific ligand molecule, effective to stably bind to said ligand, and having a detectable reporter group.

21. The method of claim 20, wherein said ligand reporter is digoxigenin or biotin and said ligand molecule is selected from the group consisting of an antibody, avidin and streptavidin.

22. The method of claim 16, wherein said examining includes detecting a fluorescent reporter bound to the reporter-labeled probe bound to the nucleic acid using either microscopy or a fluorescence activated cell sorter.

23. The method of claim 16, for localizing a selected target duplex nucleic acid sequence integrated into a host-cell genome, wherein said complex is added to the chromosomes of the cell, and said examining includes examining the chromosomes microscopically to determine the relative position of reporter-labeled probe in relation to chromosome ultrastructure.

24. A kit for the practice of the method of claim 16, comprising a RecA-protein coated single-stranded and reporter labelled DNA probe derived from the viral nucleic acid sequences, means of removing unbound complex from said structure, and means of examining the structure for the presence of the reporter labelled probe bound to the nucleic acid.

25. The kit of claim 24, where the probe is derived from hepatitis B virus sequences.

26. The kit of claim 24, where the reporter is biotin or digoxigenin.

27. The kit of claim 24, where the kit further includes means of detecting the binding of the probe to the known double-stranded viral nucleic acid sequences in a sample and said means of detection includes detecting a fluorescent reporter bound to the reporter-labeled probe bound to the nucleic acid using either microscopy or a fluorescence activated cell sorter.

28. The method of claim 16, where said fixed structures are in solution or on a slide.

29. The method of claim 16, where said allowing the complex to bind to the target sequence under non-denaturing conditions is carried out for less than 2 hours.

30. The method of claim 16, where said adding includes the addition of accessory proteins selected from the group consisting of toposiomerase I and topoisomerase II.

31. A method of detecting a single copy nucleic acid target sequence contained in a cellular or subcellular biological structure, comprising fixing the cellular or subcellular biological structure, adding to the structure, a probe complex composed of RecA protein stably bound to a single-stranded, reporter-labeled probe which is complementary to the single-copy nucleic acid target sequence, under conditions in which the complex can contact the nucleic acid target, allowing the complex to bind to the target sequence under non-denaturing conditions, removing unbound complex from said structure, and examining the structure for the presence of the reporter-labeled probe bound to the nucleic acid.

32. The method of claim 31, where said fixing is in solution or on a slide.

33. The method of claim 31, where said fixing includes incubation of the fixed structures in 10 mM Tris-acetate buffer, pH7.5, at 55°–60° C.

34. The method of claim 31, where said allowing the complex to bind to the target sequence under non-denaturing conditions is carried out for less than 2 hours.

35. The method of claim 31, where said adding includes the addition of accessory proteins selected from the group consisting of toposiomerase I and topoisomerase II.

36. The method of claim 31, wherein the complex is stabilized by the presence of a cofactor selected from the group consisting of ATPγS, GTPγS, ATP, dATP, and a combination of ATPγS and ADP.

37. The method of claim 31, wherein said probe is labeled with a ligand reporter, and said examining includes adding to the structure, specific ligand molecule, effective to stably bind to said ligand, and having a detectable reporter group.

38. The method of claim 37, wherein said ligand reporter is digoxigenin or biotin and said ligand molecule is selected from the group consisting of an antibody, avidin and streptavidin.

39. The method of claim 31, wherein said examining includes detecting a fluorescent reporter bound to the reporter-labeled probe bound to the nucleic acid using either microscopy or a fluorescence activated cell sorter.

40. The method of claim 31, for localizing a selected target duplex nucleic acid sequence integrated into a host-cell genome, wherein said complex is added to the chromosomes of the cell, and said examining includes examining the chromosomes microscopically to determine the relative position of reporter-labeled probe in relation to chromosome ultrastructure.

41. A kit for the practice of the method of claim 34, comprising a RecA-protein coated single-stranded and reporter labelled DNA probe derived from the single copy nucleic acid sequences, means of removing unbound complex from said structure, and means of examining the structure for the presence of the reporter labelled probe bound to the nucleic acid.

42. The kit of claim 41, where the probe is derived from p53 tumor suppressor gene sequences.

43. The kit of claim 41, where the reporter is biotin or digoxigenin.

44. The kit of claim 41, where the kit further includes means of detecting the binding of the probe to the single copy nucleic acid sequences in a sample and said means of detection includes detecting a fluorescent reporter bound to the reporter-labeled probe bound to the nucleic acid using either microscopy or a fluorescence activated cell sorter.

* * * * *